United States Patent
Reisner et al.

(10) Patent No.: US 9,421,228 B2
(45) Date of Patent: Aug. 23, 2016

(54) USE OF ANTI THIRD PARTY CENTRAL MEMORY T CELLS FOR ANTI-LEUKEMIA/LYMPHOMA TREATMENT

(75) Inventors: Yair Reisner, Old Jaffa (IL); Assaf Lask, Rehovot (IL); Eran Ophir, Rehovot (IL); Noga Or-Geva, Rehovot (IL); Adva Cohen, Rehovot (IL); Ran Afik, Rehovot (IL); Esther Bachar-Lustig, Rehovot (IL); Yaki Eidelstein, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/821,255

(22) PCT Filed: Sep. 8, 2011

(86) PCT No.: PCT/IL2011/000727
§ 371 (c)(1),
(2), (4) Date: Mar. 7, 2013

(87) PCT Pub. No.: WO2012/032526
PCT Pub. Date: Mar. 15, 2012

(65) Prior Publication Data
US 2013/0171108 A1    Jul. 4, 2013

Related U.S. Application Data

(63) Continuation-in-part of application No. 13/126,472, filed as application No. PCT/IL2009/001014 on Oct. 29, 2009.

(60) Provisional application No. 61/380,716, filed on Sep. 8, 2010, provisional application No. 61/193,137, filed on Oct. 30, 2008, provisional application No. 61/213,482, filed on Jun. 12, 2009.

(51) Int. Cl.
| | | |
|---|---|---|
| A01N 63/00 | (2006.01) | |
| A61K 39/00 | (2006.01) | |
| A61K 35/28 | (2015.01) | |
| C12N 5/0783 | (2010.01) | |
| C12N 5/071 | (2010.01) | |
| A61K 35/17 | (2015.01) | |
| A61K 31/517 | (2006.01) | |
| A61K 35/12 | (2015.01) | |

(52) U.S. Cl.
CPC .............. *A61K 35/28* (2013.01); *A61K 31/517* (2013.01); *A61K 35/17* (2013.01); *A61K 39/001* (2013.01); *C12N 5/0602* (2013.01); *C12N 5/0637* (2013.01); *A61K 2035/124* (2013.01); *A61K 2039/5158* (2013.01); *C12N 2501/2307* (2013.01); *C12N 2501/2315* (2013.01); *C12N 2501/2321* (2013.01)

(58) Field of Classification Search
CPC ............................. A01N 63/00; A61K 39/00
See application file for complete search history.

(56) References Cited

U.S. PATENT DOCUMENTS

| | | |
|---|---|---|
| 6,759,035 B2 | 7/2004 | Horwitz |
| 6,803,036 B1 | 10/2004 | Horwitz |
| 2002/0182211 A1 | 12/2002 | Peach et al. |
| 2003/0003083 A1 | 1/2003 | Reisner et al. |
| 2003/0022836 A1 | 1/2003 | Larsen et al. |
| 2003/0049235 A1 | 3/2003 | Reisner |
| 2003/0083246 A1 | 5/2003 | Cohen et al. |
| 2004/0022787 A1 | 2/2004 | Cohen et al. |
| 2005/0123539 A1 | 6/2005 | Rusnak |
| 2005/0214313 A1 | 9/2005 | Peach et al. |
| 2006/0269973 A1 | 11/2006 | Yee |
| 2007/0009511 A1 | 1/2007 | Hagerty et al. |
| 2008/0160022 A1 | 7/2008 | Larsen et al. |
| 2009/0022730 A1 | 1/2009 | Raulf et al. |
| 2009/0041769 A1 | 2/2009 | Peach et al. |
| 2009/0041790 A1 | 2/2009 | Rusnak |
| 2009/0068203 A1 | 3/2009 | Rusnak |
| 2009/0232774 A1 | 9/2009 | Reisner |

(Continued)

FOREIGN PATENT DOCUMENTS

| | | |
|---|---|---|
| EP | 2753351 | 7/2014 |
| WO | WO 01/49243 | 7/2001 |

(Continued)

OTHER PUBLICATIONS

International Preliminary Report on Patentability Dated Mar. 20, 2014 From the International Bureau of WIPO Re. Application No. PCT/IL2012/050354.
Official Action Dated May 8, 2014 From the US Patent and Trademark Office Re. U.S. Appl. No. 13/126,472.
Communication Pursuant to Article 94(3) EPC Dated Jan. 24, 2014 From the European Patent Office Re. Application No. 11773345.6.
Communication Pursuant to Article 94(3) EPC Dated Jan. 27, 2014 From the European Patent Office Re. Application No. 11773325.3.
International Preliminary Report on Patentability Dated Mar. 21, 2013 From the International Bureau of WIPO Re. Application No. PCT/IL2011/000726.
International Preliminary Report on Patentability Dated Mar. 21, 2013 From the International Bureau of WIPO Re. Application No. PCT/IL2011/000727.

(Continued)

*Primary Examiner* — Karen Cochrane Carlson
*Assistant Examiner* — Natalie Moss

(57) ABSTRACT

A method of treating a disease in a subject in need thereof is disclosed. The method comprising: (a) transplanting a non-syngeneic cell or tissue graft to the subject; and (b) administering to the subject a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, and further wherein the cells are either: (i) non-syngeneic with both the subject and the graft; or (ii) non-syngeneic with the graft and syngeneic with the subject, thereby treating the subject.

19 Claims, 9 Drawing Sheets
(9 of 9 Drawing Sheet(s) Filed in Color)

(56) References Cited

U.S. PATENT DOCUMENTS

| | | |
|---|---|---|
| 2010/0022627 A1 | 1/2010 | Scherer |
| 2010/0041602 A1 | 2/2010 | Hagerty et al. |
| 2010/0049935 A1 | 2/2010 | Pichumani et al. |
| 2010/0166756 A1 | 7/2010 | Cohen et al. |
| 2010/0183612 A1 | 7/2010 | Peach et al. |
| 2011/0212071 A1 | 9/2011 | Reisner et al. |
| 2013/0183322 A1 | 7/2013 | Reisner et al. |
| 2014/0212398 A1 | 7/2014 | Reisner et al. |

FOREIGN PATENT DOCUMENTS

| | | | |
|---|---|---|---|
| WO | WO 02/43651 | 6/2002 | |
| WO | WO 02/102971 | 12/2002 | |
| WO | WO 2005/092380 | 10/2005 | |
| WO | WO 2006/041763 | 4/2006 | |
| WO | WO 2007/023491 | 3/2007 | |
| WO | WO 2010/049935 | 5/2010 | |
| WO | WO 2010/049935 A1 * | 5/2010 | ............. A61K 39/00 |
| WO | WO 2012/032525 | 3/2012 | |
| WO | WO 2012/032526 | 3/2012 | |
| WO | WO 2013/035099 | 3/2013 | |

OTHER PUBLICATIONS

Office Action Dated Apr. 15, 2013 From the Israel Patent Office Re. Application No. 212587 and Its Translation Into English.
Written Opinion and Search Report Dated Feb. 28, 2014 From the Intellectual Property Office of Singapore Issued by the Austrian Patent Office Re. Application No. 201301743-9.
Restriction Official Action Dated Mar. 13, 2013 From the US Patent and Trademark Office Re. U.S. Appl. No. 13/126,472.
Official Action Dated Aug. 1, 2013 From the US Patent and Trademark Office Re. U.S. Appl. No. 13/126,472.
Office Action Dated May 14, 2014 From the Israel Patent Office Re. Application No. 212587 and Its Translation Into English.
Office Action Dated Apr. 29, 2014 From the State Intellectual Property Office of the People's Republic of China Re. Application No. 201180053858.9 and Its Translation into English.
Search Report Dated Apr. 29, 2014 From the State intellectual Property Office of the People's Republic of China Re. Application No. 201180053858.9 and Its Translation Into English.
Communication Pursuant to Rule 114(2) EPC (Third Party Observation) Dated Sep. 26, 2014 From the European Patent Office Re. Application No. 12769743.1.
Dutton et al. "T Cell Memory", Annual Review of Immunology, 16: 201-223, 1998.
Examination Report Dated Jan. 8, 2015 From the Intellectual Property Office of New Zealand Re. Application No. 622749.
Communication Pursuant to Article 94(3) EPC Dated Jun. 4, 2014 From the European Patent Office Re. Application No. 09764302.7.
Weninger et al. "Migratory Properties of Naive, Effector, and Memory CD8+ T Cells", Journal of Experimental Medicine, 12(6): 953-966, Oct. 1, 2001.
Restriction Official Action Dated Aug. 14, 2014 From the US Patent and Trademark Office Re. U.S. Appl. No. 13/821,269.
Search Report and Written Opinion Dated Oct. 10, 2014 From the Intellectual Property Office of Singapore Re. Application No. 11201400513.
Huarte et al. "Ex Vivo Expansion of Tumor Specific Lymphocytes With IL-15 and IL-21 for Adoptive Immunotherapy in Melanoma", Cancer Letters, 285: 80-88, 2009. Abstract, p. 80, Left Right col., 2nd Para, Section 2.4.
Li et al. "IL-21 Influences the Frequency, Phenotype, and Affinity of the Antigen-Specific CD8 T Cell Response", The Journal of Immunology, 175: 2261-2269, 2005. Abstract, Materials and Methods: Induction of Human Ag-Specific CD8+ T Cells.
Decision on Rejection Dated Dec. 2, 2015 From the State Intellectual Property Office of the People's Republic of China Re. Application No. 201180053858.9 and Its Translation Into English.
Communication Pursuant to Article 94(3) EPC Dated Jan. 26, 2015 From the European Patent Office Re. Application No. 12769743.1.
Notification of Office Action and Search Report Dated Jan. 23, 2015 From the State Intellectual Property Office of the People's Republic of China Re. Application No. 201280054739.X.
Translation Dated Feb. 8, 2015 of Notification of Office Action and Search Report Dated Jan. 23, 2015 From the State Intellectual Property Office of the People's Republic of China Re. Application No. 201280054739.X.
Examination Report Dated Feb. 2, 2016 From the Intellectual Property Office of Singapore Re. Application No. 11201400513P.
Official Action Dated Feb. 12, 20106 From the US Patent and Trademark Office Re. U.S. Appl. No. 14/343,053.
Roncarolo et al. "Regulatory T-Cell Immunotherapy for Tolerance to Self Antigens and Alloantigens in Humans", Nature Reviews Immunology, 7(8): 585-598, Aug. 2007.
Santegoets et al. "In Vitro Priming of Tumor-Specific Cytotoxic T Lymphocytes Using Allogeneic Dendritic Cells Derived From the Human MUTZ-3 Cell Line", Cancer Immunol Immunother, 55(12): 1480-1490, Published Online Feb. 9, 2006.
Zeng et al. "Synergy of IL-21 and IL-15 in Regulating CD8+ T Cell Expansion and Function", The Journal of Experimental Medicine, 201(1): 139-148, Jan. 3, 2005.
Communication Pursuant to Article 94(3) EPC Dated Dec. 14, 2012 From the European Patent Office Re. Application No. 09764302.7.
International Preliminary Report on Patentability Dated May 12, 2011 From the International Bureau of WIPO Re.: Application No. PCT/IL2009/001014.
International Search Report and the Written Opinion Dated Mar. 7, 2012 From the international Searching Authority Re.: Application No. PCT/IL2011/000727.
International Search Report and the Written Opinion Dated Feb. 16, 2010 From the International Searching Authority Re.: Application No. PCT/IL2009/001014.
International Search Report and the Written Opinion Dated Jun. 27, 2012 From the International Searching Authority Re.: Application No. PCT/IL2011/000726.
International Search Report and the Written Opinion Dated Jan. 28, 2013 From the International Searching Authority Re. Application No. PCT/IL2012/050354.
Translation of Office Action Dated Dec. 27, 2012 From the State Intellectual Property Office of the People's Republic of China Re. Application No. 200980153053.4.
Translation of Search Report Dated Dec. 27, 2012 From the State Intellectual Property Office of the People's Republic of China Re. Application No. 200980153053.4.
Albrecht et al. "IL-21-Treated Naive CD45RA+ CD8+ T Cells Repressant a Reliable Source for Producing Leukemia-Reactive Cytotoxic T Lymphocytes With High Proliferative Potential and Early Differentiation Phenotype", Cancer Immunology, Immunotherapy: CII, XP002689103, 60(2): 235-248, Feb. 2011. Abstract.
Arditti et al. "Eradication of B-CLL by Autologous and Allogeneic Host Nonreactive Anti-Third-Party CTLs", Blood, 105(8): 3365-3371, Apr. 15, 2005.
Aversa et al. "Full Haplotype-Mismatched Hematopoietic Stem-Cell Transplantation: A Phase II Study in Patients With Acute Leukemia at High Risk of Relapse", Journal of Clinical Oncology, 23(15): 3447-3454, May 20, 2005.
Aversa et al. "Successful Engraftment of T-Cell-Depleted Haploidentical 'Three-Loci' Incompatible Transplants in Leukemia Patients by Addition of Recombinant Human Granulocyte Colony-Stimulating Factor-Mobilized Peripheral Blood Progenitor Cells to Bone Marrow Inoculum", Blood, 84(4): 3948-3955, Dec. 1, 1994.
Aversa et al. "Treatment of High-Risk Acute Leukemia With T-Cell-Depleted Stem Cells From Related Donors With One Fully Mismatched HLA Haplotype", The New England Journal of Medicine, 339(17): 1186-1193, Oct. 22, 1998.
Aviner et al. "Large-Scale Preparation of Human Anti-Third-Party Veto Cytotoxic T Lymphocytes Depleted of Graft-Versus-Host Reactivity: A New Source for Graft Facilitating Cells in Bone Marrow Transplantation", Human Immunology, 66: 644-652, 2005.
Bachar-Lustig et al. "Anti-Third-Party Veto CTLs Overcome Rejection of Hematopoietic Allografts: Synergism With Rapamycin and BM Cell Dose", Blood, 102(6): 1943-1950, Sep. 15, 2003.

(56) References Cited

OTHER PUBLICATIONS

Bachar-Lustig et al. "Megadose of T Cell-Depleted Bone Marrow Overcomes MHC Barriers in Sublethally Irradiated Mice", Nature Medicine, 1(12): 1268-1273, Dec. 1995.
Grigg et al. "Graft-Versus-Lymphoma Effects: Clinical Review, Policy Proposal, and Immunobiology", Biology of Blood and Marrow Transplantation, 10: 579-590, 2004.
Gur et al. "Immune Regulatory Activity of CD34+ Progenitor Cells: Evidence for a Deletion-Based Mechanism Mediated by TNF-{Alpha}", Blood, 105(6): 2585-2593, Mar. 15, 2005.
Gur et al. "Tolerance Induction by Megadose Hematopoietic Progenitor Cells: Expansion of Veto Cells by Short-Term Culture of Purified Human CD34+ Cells", Blood, 99(11): 4174-4181, Jun. 1, 2002.
Handgretinger et al. "Megadose Transplantation of Purified Peripheral Blood CD34+ Progenitor Cells From HLA-Mismatched Parental Donors in Children", Bone Marrow Transplantation, 27: 777-783, 2001.
Harwerth et al. "Monoclonal Antibodies Directed to the ErbB-2 Receptor Inhibit in Vivo Tumour Cell Growth", British Journal of Cancer, 68(6): 1140-1145, Dec. 1993.
Hecht et al. "Embryonic Pig Pancreatic Tissue for the Treatment of Diabetes in a Nonhuman Primate Model", Proc. Natl. Acad. Sci. USA, PNAS, XP009122169, 106(21): 8659-8664, May 26, 2009. p. 8663, col. 1, Para 2.
Ho et al. "Adoptive Therapy With CD8+ T Cells: It May Get by With a Little Help From Its Friends", the Journal of Clinical Investigation, 110(10): 1415-1417, Nov. 2002.
Kawai et al. "HLA-Mismatched Renal Transplantation Without Maintenance Immunosuppression", The New England Journal of Medicine, XP002562461, 358(4): 353-361, Jan. 24, 2008. p. 353-354, col. 1, Para 2, Table 1.
Lapidot et al. "Enhancement by Dimethyl Myleran of Donor Type Chimerism in Murine Recipients of Bone Marrow Allografts", Blood, 73(7): 2025-2032, May 15, 1989.
Lapidot et al. "Enhancement by Dimethyl Myleran of Donor type Chimerism in Murine Resipients of Bone Marrow Allografts", Blood, 73(7): 2025-2032, May 15, 1989.
Lask et al. "TCR Independent Killing of B Cell Malignancies by Anti-3rd Party CTLs: Rapid Conjugate Formation via ICAM1-LFA1 Leads to Slow induction of Apoptosis Upon MHC-CD8 Engagement", Journal of Immunology, XP009156306, 187(4): 2006-2014, Aug. 15, 2011.
Markley et al. "IL-7 and IL-21 Are Superior to IL-2 and IL-15 in Promoting Human T Cell-Mediated Rejection of Systematic Lymphoma in Immunodeficient Mice", Blood, XP009165652, 115(17): 3508-3519, Apr. 29, 2010. p. 3509, col. 2, Para 2.
Ophir et al. "Induction of Tolerance in Organ Recipients by Hematopoietic Stem Cell Transplantation", International Immunopharmacology, XP026088865, 9(6): 694-700, Jun. 1, 2009. Figs.3, 6.
Ophir et al. "Induction of Tolerance to Bone Marrow Allografts by Donor-Derived Host Nonreactive Ex Vivo Induced Central Memory CD8 T Cells", Blood, XP009165643, 115(10): 2095-2104, Mar. 11, 2010. p. 2096, col. 1, Para 2.
Ophir et al. "Induction of Transplantation Tolerance in Haploidenical Transplantation Under Reduced Intensity Conditioning: The Role of Ex-Vivo Generated Donor CD8+ T Cells With Central Memory Phenotype", Best Practice & Research Clinical Haematology, XP002829486, 24(3): 393-401, Jul. 13, 2011. p. 396, Fig.3.
Pilat et al. "Treg-Therapy Allows Mixed Chimerism and Transplantation Tolerance Without Cytoreductive Conditioning", American Journal of Transplantation, 10: 751-762, 2010.
Rachamim et al. "Tolerance Induction by 'Megadose' Hematopoietic Transplant: Donor-Type Human CD34 Stem Cells Induce Potent Specific Reduction of Host Anti-Donor Cytotoxic T Lymphcyte Precursors in Mixed Lymphocyte Culture", Transplantation, 65(10): 1386-1393, May 27, 1998.
Rachamim et al. "Tolerance Induction by 'Megadose' Hematopoietic Transplants. Donor-Type CD34 Stem Cells Induce Potent Specific Reduction of Host anti-Donor Cytotoxic T Lymphocyte Precursors in Mixed Lymphocyte Culture", Transplantation, 65(10): 1386-1393, May 27, 1998.
Reich-Zeliger et al. "Anti-Third Party CD8+ CTLs as Potent Veto Cells: Coexpression of CD8 and FasL Is a Prerequisite", Immunity, 13: 507-515, Oct. 2000.
Reich-Zeliger et al. "Tolerance Induction by Veto CTLs in the TCR Transgenic 2C Mouse Model. I. Relative Reactivity of Different Veto Cells", The Journal of Immunology, 173: 6654-6659, 2004.
Reisner et al. "Bone Marrow Transplantation Across HLA Barriers by Increasing the Number of Transplanted Cells", Immunology Today, 16(9): 437-440, 1995.
Reisner et al. "Demonstration of Clonable Alloreactive Host T Cells in a Primate Model for Bone Marrow Transplantation", Proc. Natl. Acad. Sci. USA, 83: 4012-415, Jun. 1986.
Reisner et al. "Stem Cell Escalation Enables HLA-Disparate Haematopoietic Transplants in Leukaemia Patients", Immunology Today, 20(8): 343-347, Aug. 1999.
Scandling et al. "Tolerance and Chimerism After Renal and Hematopoietic-Cell Tranplantation", The New England Journal of Medicine, XP002562462, 358(4): 362-368, Jan. 24, 2008. p. 363-365, Fig.3, Abstract, p. 362, Para 1, 3—p. 363, Left col., Para 2, Right col., OPara 2, 4, p. 365, Left col., Para 2, p. 367, Discussion, Figs.2, 3.
Tehorsh-Yutsis et al. "Pig Embryonic Pancreatic Tissue as a Source for Transplantation in Diabetes. Transient Treatment With Anit-LFA1, Anit-CD48, and FTY720 Enables Long-Term Graft Maintenance in Mice With Only Mild Ongoing Immunosuppression", Diabetes, XP009122170, 58(7): 1585-1594, Jul. 1, 2009. Figs.5, 7, Table 1.
Uharek et al. "Influence of Cell Dose and Graft-Versus-Host Reactivity on Rejection Rates After Allogeneic Bone Marrow Transplantation", Blood, 79(6): 1612-1621, Mar. 15, 1992.
Wherry et al. "Lineage Relationship and Protective Immunity of Memory CD8 T Cell Subsets", Nature Immunology, XP002562463, 4(3): 225-234, Mar. 2003. p. 232-233, Figs.1-4.
Woelfl et al. "Primed Tumor-Reactive Multifunctional CD62L+ Human CD8+ T Cells for Immunotherapy", Cancer Immunology, Immunotherapy, 60(2): 173-186, Feb. 2011.
Xie "The Development of the PBSC Transplantation", Railway Medical Journal, 29(5): 281-283, Jan. 31, 2001. & English Translation.
Yang et al. "In Vitro Generated Anti-Tumor T Lymphocytes Exhibit Distinct Subsets Mimicking in Vivo Antigen-Experienced Cells", Cancer Immunology, Immunotherapy: CII, XP009165653, 60(5): 739-749, May 2011.
Communication Pursuant to Article 94(3) EPC Dated Mar. 24, 2015 From the European Patent Office Re. Application No. 11773325.3.
Office Action Dated Mar. 18, 2015 From the State Intellectual Property Office of the People's Republic of China Re. Application No. 201180053858.9 and Its Translation Into English.
Written Opinion Dated Feb. 17, 2015 From the Intellectual Property Office of Singapore Issued by the Austrian Patent Office Re. Application No. 201301743-9.
Written Opinion Dated Jun. 11, 2015 From the Intellectual Property Office of Singapore Re. Application No. 11201400513P.
Fujiwara "Adoptive Immunotherapy for Hematological Malignancies Using T Cells Gene-Modified to Express Tumor Antigen-Specific Receptors", Pharmaceuticals, 7: 1049-1068, Dec. 15, 2014.
Notice of Reason for Rejection Dated Aug. 4, 2015 From the Japanese Patent Office Re. Application No. 2013-527738 and Its Translation Into English.
Restriction Official Action Dated Oct. 20, 2015 From the US Patent and Trademark Office Re. U.S. Appl. No. 14/343,053.
Communication Pursuant to Article 94(3) EPC Dated Oct. 21, 2015 From the European Patent Office Re. Application No. 12769743.1.
Office Action Dated Oct. 12, 2015 From the Israel Patent Office Re. Application No. 225102 and Its Translation Into English.

(56) References Cited

OTHER PUBLICATIONS

Office Action Dated Sep. 23, 2015 From the State Intellectual Property Office of the People's Republic of China Re. Application No. 201280054739.X and Its Translation Into English.

Examination Report Dated Oct. 15, 2015 From the Intellectual Property Office of Singapore Issued by the Austrian Patent Office Re. Application No. 201301743-9.

Official Action Dated Nov. 19, 2015 From the US Patent and Trademark Office Re. U.S. Appl. No. 13/126,472.

* cited by examiner

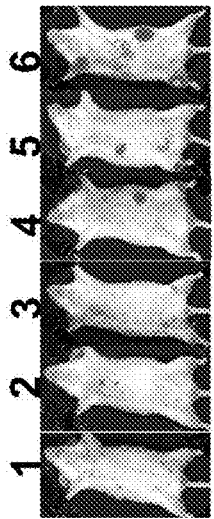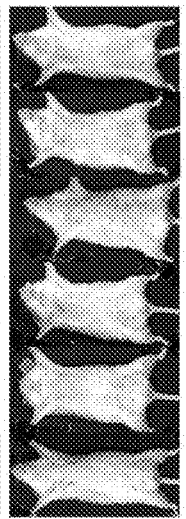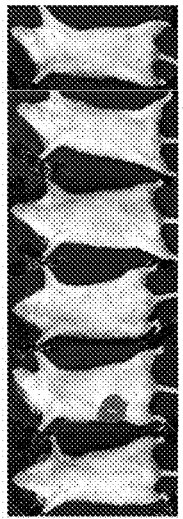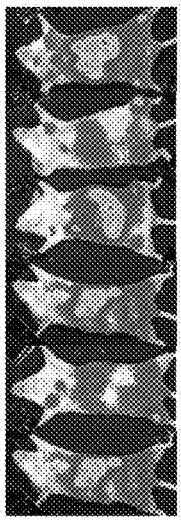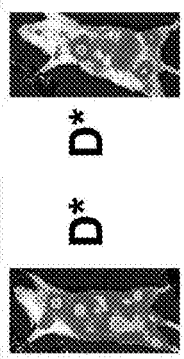
FIG. 1A Day 14
FIG. 1B Day 21
FIG. 1C Day 28
FIG. 1D Day 38
FIG. 1E
FIG. 1F
FIG. 1G
FIG. 1H
A20 only
A20+ $1\times10^7$ Syn TCM
D* - Animal died from the tumor

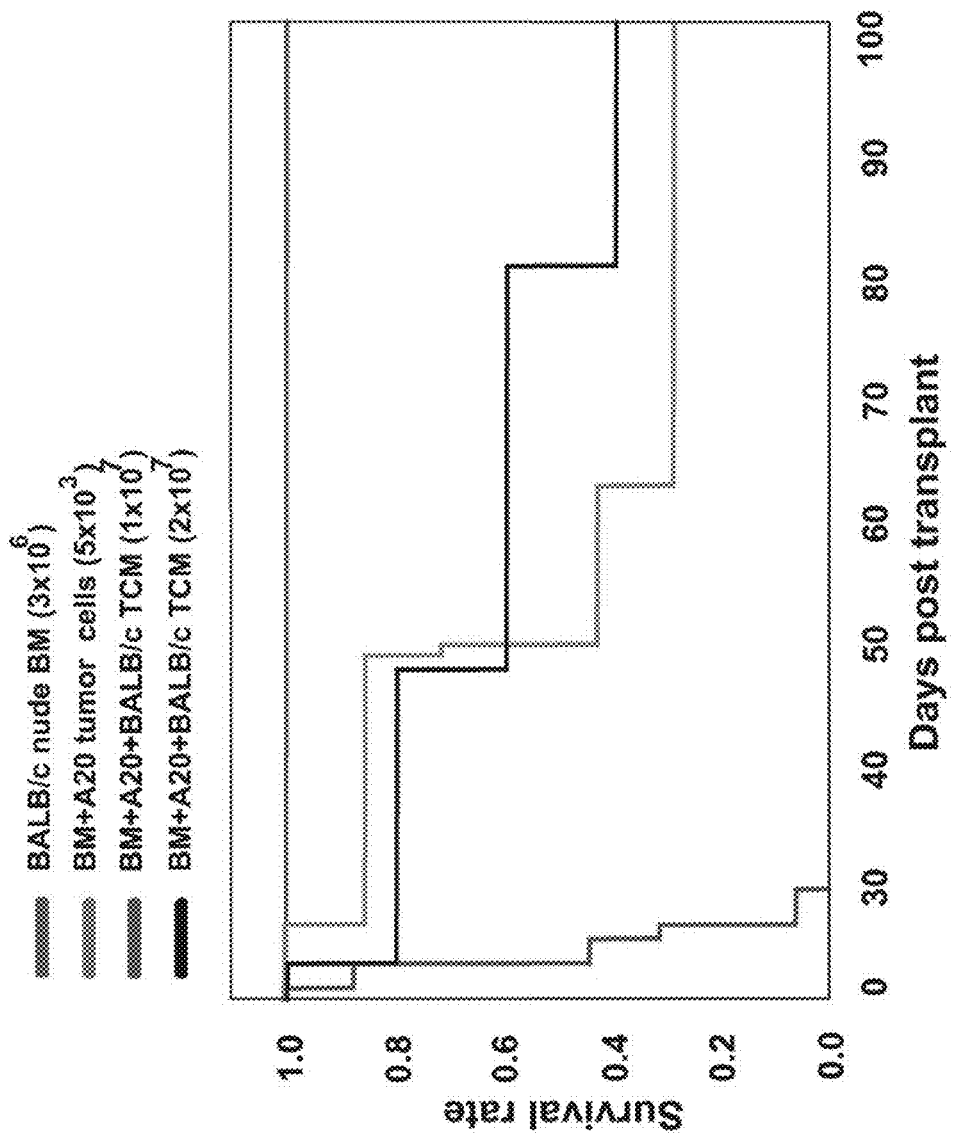

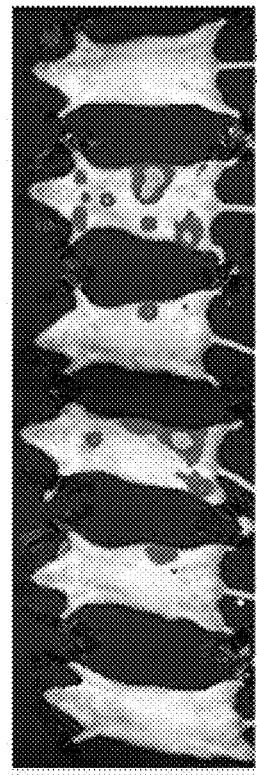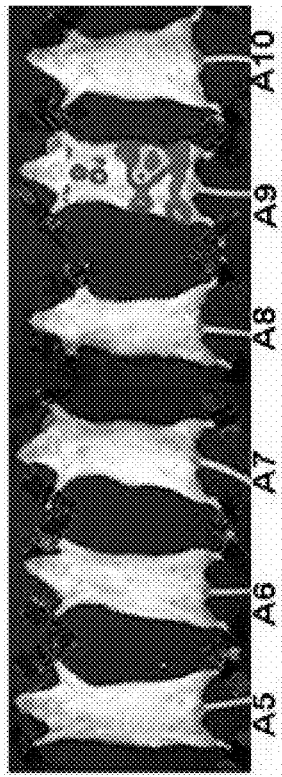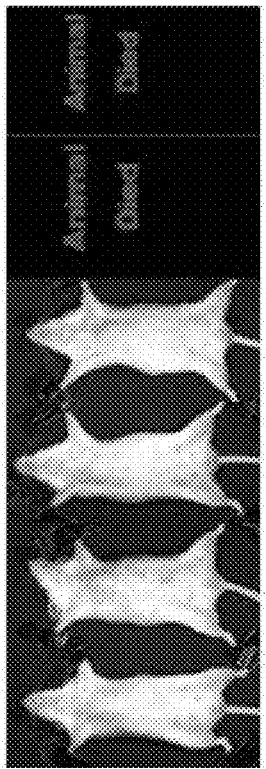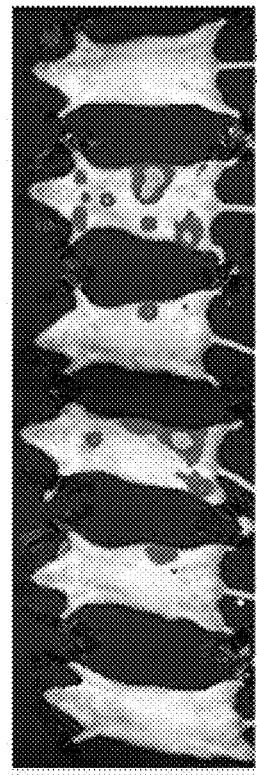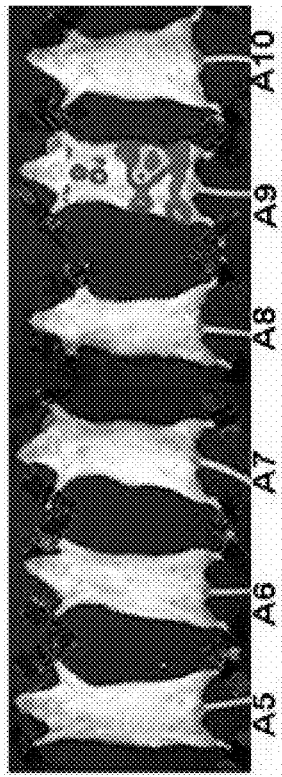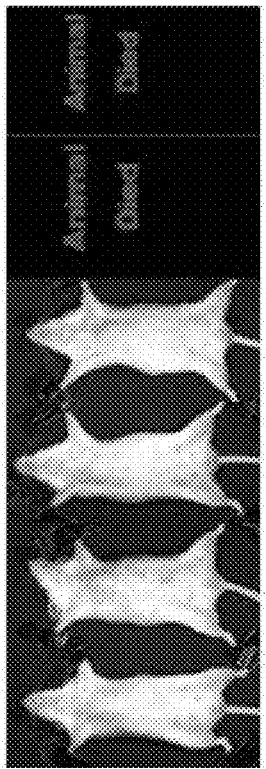

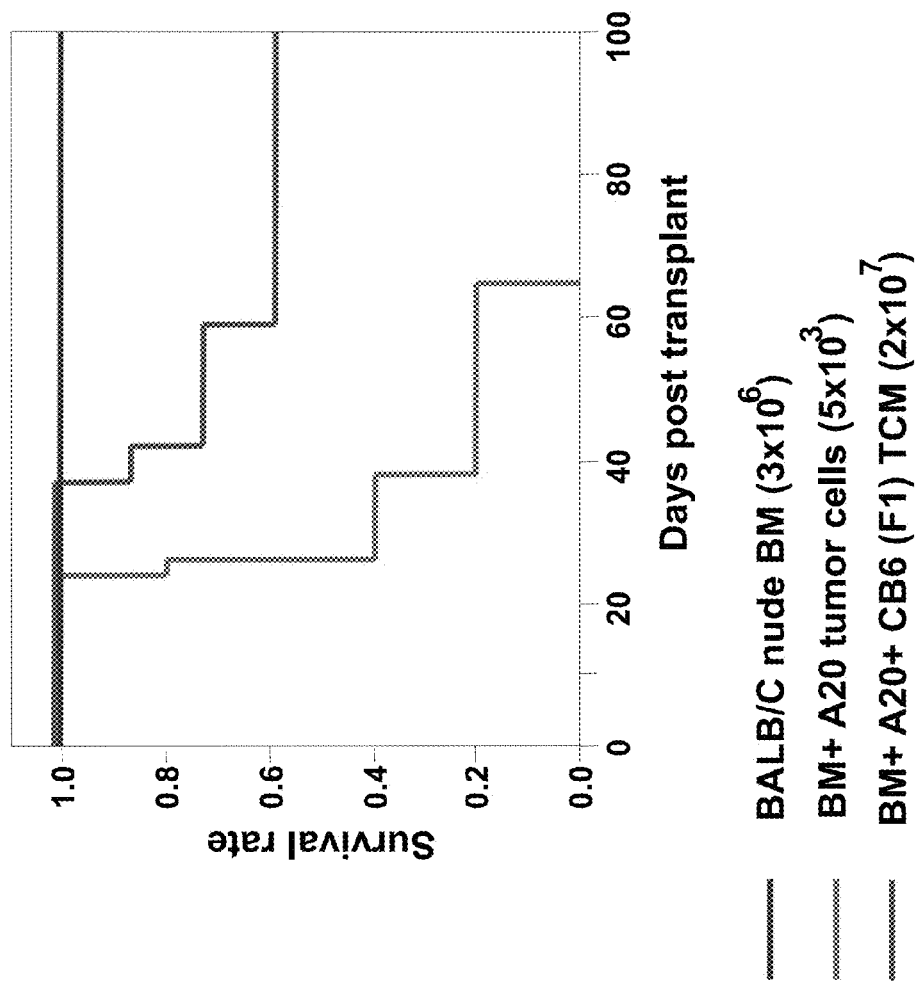

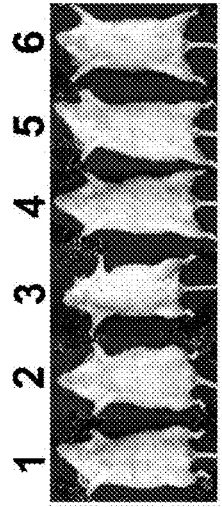
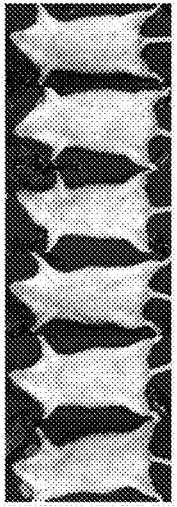
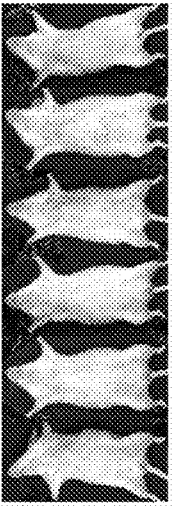
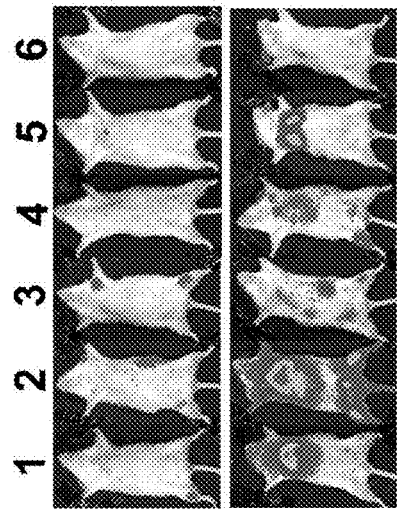
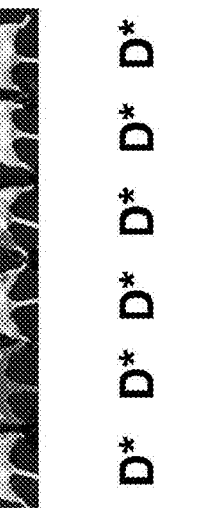
FIG. 3E
FIG. 3F
FIG. 3G
FIG. 3H
A20+5x10$^6$ allo TCM
A20 only
D* D* D* D* D*
D* D* D* D* D*
FIG. 3A Day 13
FIG. 3B Day 21
FIG. 3C Day 28
FIG. 3D Day 35
D*-Animal died from the tumor

USE OF ANTI THIRD PARTY CENTRAL MEMORY T CELLS FOR ANTI-LEUKEMIA/LYMPHOMA TREATMENT

This application is a National Phase of PCT Patent Application No. PCT/IL2011/000727 having International filing date of Sep. 8, 2011, which claims the benefit of priority under 35 USC §119(e) of U.S. Provisional Patent Application No. 61/380,716 filed on Sep. 8, 2010. The contents of the above applications are all incorporated herein by reference. This application is also a Continuation-in-Part (CIP) of U.S. patent application Ser. No. 13/126,472 filed on Apr. 28, 2011, which is a National Phase of PCT Patent Application No PCT/IL2009/001014 having International filing date of Oct. 29, 2009, which claims the benefit of priority under 35 USC §119(e) of U.S. Provisional Patent Application Nos. 61/193,137 filed on Oct. 30, 2008 and 61/213,482 filed on Jun. 12, 2009.

FIELD AND BACKGROUND OF THE INVENTION

The present invention, in some embodiments thereof, relates to non-graft versus host disease (GVHD) inducing anti-third party cells comprising a central memory T-lymphocyte phenotype and, more particularly, but not exclusively, to the use of same for graft versus leukemia/lymphoma treatment.

Treatment options for patients with hematological malignancies such as non-Hodgkin lymphoma (NHL) are many and varied. These modern treatment protocols lead to complete remission (CR) in a considerable proportion of the patients. However, many of these patients ultimately relapse, implying that residual tumor cells remain in patients achieving a clinical CR. To address this challenge donor lymphocyte infusion (DLI) endowed with graft-versus-leukemia/lymphoma (GVL) reactivity are currently being developed. In particular, progress has been made in the context of allogeneic bone marrow transplantation (BMT) in conjunction with DLI after transplantation [Grigg A and Ritchie D, Biol Blood Marrow Transplant (2004) 10: 579-590]. Thus, it has been demonstrated that donor CD8+ T cells present in the stem cell graft or in DLI have the added benefit of GVL effect that can kill residual malignant cells [Ho W Y et al., J Clin Invest. (2002) 110: 1415-1417]. However, this benefit is offset by graft-versus-host disease (GVHD), associated with CD8 T cells, which adversely impact transplant-related mortality.

Previous work done by the present inventors has shown that ex-vivo stimulation of murine CD8+ T cells against 3rd-party stimulators, under IL-2 deprivation, leads to selective growth of 3rd-party restricted CD8+ cytotoxic T lymphocyte (CTL) clones which can facilitate T cell depleted BMT (TDBMT) engraftment without causing GVHD [Bachar-Lustig E. et al., Blood (2003) 102:1943-1950; Reich-Zeliger S. et al., Immunity (2000) 13: 507-515]. Recently, the present inventors demonstrated that activated anti-3rd party CD8+ cells with central memory phenotype (Tcm), can further support and improve bone marrow (BM) engraftment, likely due to the improved lymph node homing of the Tcm cells, their proliferative capacity and prolonged persistence in BMT recipients [Ophir E et al., Blood (2010) 115: 2095-2104].

Furthermore, the present inventors have shown that in humans, anti-3rd party CTLs, although depleted of alloreactivity, exhibit potent in-vitro killing of B-CLL and different types of primary lymphoma cells [Lask A et al. (submitted 2010); Arditti F D et al., Blood (2005) 105:3365-3371]. This unique form of GVL was shown to be independent of TCR recognition and it was found to be mediated both by autologous and by allogeneic anti-3rd party CTLs. Furthermore, this TCR independent killing of B cell malignancies by anti-3rd party CTLs was shown to be mediated via a rapid adhesion through ICAM1-LFA1 binding, followed by slow induction of apoptosis upon a critical interaction between CD8 on the CTL and MHC class I on the tumor cell. Moreover, the killing was shown to be independent of the classical CTLs death molecules: FASL, perforin, TNF, and Trail [Lask A et al., supra].

Additional background art includes WO/2010/049935.

SUMMARY OF THE INVENTION

According to an aspect of some embodiments of the present invention there is provided a method of treating a disease in a subject in need thereof, the method comprising: (a) transplanting a non-syngeneic cell or tissue graft to the subject; and (b) administering to the subject a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, and further wherein the cells are either: (i) non-syngeneic with both the subject and the graft; or (ii) non-syngeneic with the graft and syngeneic with the subject, thereby treating the subject.

According to an aspect of some embodiments of the present invention there is provided a use of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, as an adjuvant treatment for eradication of a disease in a subject who has been transplanted with a non-syngeneic cell or tissue graft, wherein the cells are either: (i) non-syngeneic with both the subject and the graft; or (ii) non-syngeneic with the graft and syngeneic with the subject.

According to an aspect of some embodiments of the present invention there is provided an isolated population of cells comprising non-GVHD inducing anti-third party cells having a central memory T-lymphocyte (Tcm) phenotype, the cells being tolerance-inducing cells and capable of homing to the lymph nodes following transplantation, and further wherein the cells are either: (i) non-syngeneic with both a host subject and a graft, wherein the subject and the graft are non-syngeneic; or (ii) non-syngeneic with a graft and syngeneic with a host subject, wherein the subject and the graft are non-syngeneic.

According to an aspect of some embodiments of the present invention there is provided a method of treating a disease in a subject in need thereof, the method comprising: (a) transplanting immature hematopoietic cells to the subject; and (b) administering to the subject a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, wherein when the immature hematopoietic cells are syngeneic with the subject, the isolated population of cells are selected syngeneic with the subject or non-syngeneic with the subject.

According to an aspect of some embodiments of the present invention there is provided a method of treating a disease in a subject in need thereof, the method comprising: (a) transplanting immature hematopoietic cells to the subject;

and (b) administering to the subject a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, wherein when the immature hematopoietic cells are non-syngeneic with the subject, the isolated population of cells are selected syngeneic with the subject or non-syngeneic with both the subject and the immature hematopoietic cells.

According to some embodiments of the invention the non-syngeneic cell or tissue graft is derived from a donor selected from the group consisting of an HLA identical donor and an HLA non-identical donor.

According to some embodiments of the invention the subject and the donor are both humans.

According to some embodiments of the invention the subject is a human subject.

According to some embodiments of the invention the cell or tissue graft is non-autologous and the isolated population of cells are autologous.

According to some embodiments of the invention the cell or tissue graft and the isolated population of cells are from different donors.

According to some embodiments of the invention the disease comprises a malignancy.

According to some embodiments of the invention the malignancy comprises a B cell malignancy.

According to some embodiments of the invention the malignancy comprises a leukemia.

According to some embodiments of the invention the malignancy comprises a lymphoma.

According to some embodiments of the invention the graft comprises bone marrow cells.

According to some embodiments of the invention the bone marrow cells comprise immature hematopoietic cells.

According to some embodiments of the invention the immature hematopoietic cells are non-syngeneic with the subject, the isolated population of cells are syngeneic with the subject.

According to some embodiments of the invention the immature hematopoietic cells are non-autologous and the isolated population of cells are autologous.

According to some embodiments of the invention when the immature hematopoietic cells are non-syngeneic with the subject, the isolated population of cells are non-syngeneic with both the subject and with the graft.

According to some embodiments of the invention the immature hematopoietic cells and the isolated population of cells are from different donors.

According to some embodiments of the invention the method further comprises administering at least one immunosuppressant drug to the subject.

According to some embodiments of the invention the subject is further conditioned under sublethal, lethal or supralethal conditioning prior to step (a).

According to some embodiments of the invention step (a) and step (b) are effected concomitantly.

According to some embodiments of the invention step (b) is effected prior to step (a).

According to some embodiments of the invention step (b) is effected one day after step (a).

According to some embodiments of the invention the central memory T-lymphocyte (Tcm) phenotype comprises a $CD8^+/CD62L^+$ signature.

According to some embodiments of the invention at least 50% of the isolated population of cells have the signature.

According to some embodiments of the invention the lymph nodes comprise peripheral lymph nodes.

According to some embodiments of the invention the lymph nodes comprise mesenteric lymph nodes.

According to some embodiments of the invention the cells non-syngeneic with the graft and syngeneic with the subject comprise autologous cells.

According to some embodiments of the invention the cells non-syngeneic with the graft and syngeneic with the host subject are autologous.

According to some embodiments of the invention the immature hematopoietic cells and the isolated population of cells are autologous.

According to some embodiments of the invention the immature hematopoietic cells are autologous and the isolated population of cells are non-autologous.

According to some embodiments of the invention the immature hematopoietic cells are non-autologous and the isolated population of cells are autologous.

According to some embodiments of the invention the immature hematopoietic cells and the isolated population of cells are from different donors.

According to some embodiments of the invention the anti-third party cells having a central memory T-lymphocyte (Tcm) phenotype, the cells being tolerance-inducing cells and capable of homing to the lymph nodes following transplantation are generated by: (a) contacting peripheral blood mononuclear cells (PBMC) with a third party antigen or antigens in the presence or absence of IL-21 under conditions which allow elimination of GVH reactive cells; and (b) culturing the cells resulting from step (a) in the presence of IL-15 in an antigen free environment under conditions which allow proliferation of cells comprising the central memory T-lymphocyte (Tcm) phenotype, thereby generating the isolated population of cells.

According to some embodiments of the invention the conditions which allow elimination of GVH reactive cells comprise culturing for 1-5 days.

According to some embodiments of the invention the conditions which allow elimination of GVH reactive cells comprise 1-5 days in a culture deprived of cytokines.

According to some embodiments of the invention the third party antigen or antigens comprise dendritic cells.

According to some embodiments of the invention the third party antigen or antigens is selected from the group consisting of third party cells, a cell antigen, a viral antigen, a bacterial antigen, a protein extract, a purified protein and a synthetic peptide presented by autologous presenting cells, non-autologous presenting cells or on an artificial vehicle or artificial antigen presenting cell.

According to some embodiments of the invention the conditions which allow proliferation of cells further comprise IL-7.

According to some embodiments of the invention the culturing in the presence of IL-15 is effected for 3-30 days.

According to some embodiments of the invention the culturing in the presence of IL-15 is effected for 6-30 days.

According to some embodiments of the invention the culturing in the presence of IL-15 is effected for 3-20 days.

According to some embodiments of the invention the conditions which allow proliferation of cells comprise culturing for 3-10 days.

According to some embodiments of the invention the conditions which allow proliferation of cells comprise culturing for 3-7 days.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-I depict inhibition of tumor relapse by syngeneic derived anti-$3^{rd}$ party Tcm cells after syngeneic bone marrow transplantation. Lethally irradiated (8 Gy) BALB/c mice (H-$2^d$) received intravenously a transplant of $3 \times 10^6$ syngeneic T cell depleted bone marrow (BALB/c-NUDE (H-$2^d$) in the presence or absence of $5 \times 10^3$ A20-luc lymphoma cells (day 0). Mice were then intravenously injected with or without the indicated numbers of BALB/c derived anti-$3^{rd}$ party Tcm cells (indicated as leukemia cells+Tcm, n=7; or with only leukemia cells, n=7, respectively) on day +1. FIGS. 1A-H are pictures depicting tumor growth monitored by bioluminescence imaging (BLI) from day 14 in weekly intervals; FIG. 1I is a graph depicting the survival rate of the animals from the different treatment groups. X-axis indicates days after tumor cell injection and the y-axis indicates the proportion of recipient mice surviving.

FIGS. 2A-G depict inhibition of tumor relapse by F1 derived anti-$3^{rd}$ party CD8 T cells after syngeneic bone marrow transplantation. Lethally irradiated (8 Gy) BALB/c mice (H-$2^d$) received intravenously a transplant of $3 \times 10^6$ syngeneic T cell depleted bone marrow cells (BALB/c-NUDE (H-$2^d$) in the presence or absence of $5 \times 10^3$ A20-luc lymphoma cells (day 0). Mice were then intravenously injected with or without $2 \times 10^7$ F1 derived anti-$3^{rd}$ party Tcm cells (Leukemia cells+Tcm, n=7) or without (Leukemia cells alone, n=5) on day +1; FIGS. 2A-F are pictures depicting tumor growth monitored by BLI from day 14 in weekly intervals. FIG. 2G is a graph depicting the survival rate of the animals from the different treatment groups. X-axis indicates days after tumor cell injection and the y-axis indicates the proportion of recipient mice surviving.

Figure 3I:
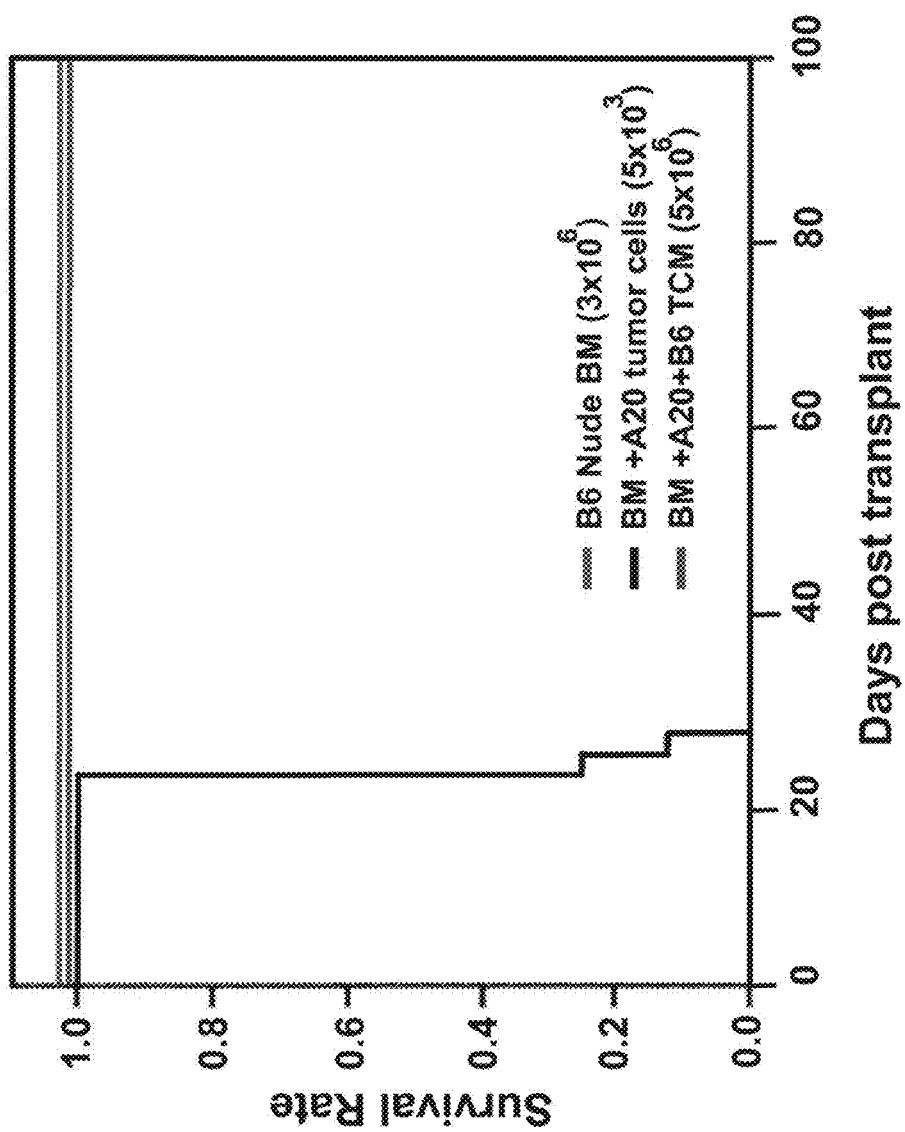

FIGS. 3A-I depict inhibition of tumor relapse by allogeneic derived anti-$3^{rd}$ party Tcm cells after allogeneic bone marrow transplantation. Lethally irradiated (8 Gy) BALB/c (H-$2^d$) mice received intravenously a transplant of $3 \times 10^6$ allogeneic T cell depleted bone marrow cells (C57BL/6-NUDE (H-$2^b$) in the presence or absence of $5 \times 10^3$ A20-luc lymphoma cells (day 0). Mice were then intravenously injected with C57BL/6 derived cells (on day +1). FIGS. 3A-H are pictures depicting tumor growth monitored by BLI from day 13 in weekly intervals; FIG. 3I is a graph depicting the survival rate of the animals from the different treatment groups. X-axis indicates days after tumor cell injection and the y-axis indicates the proportion of recipient mice surviving.

Figure 4A:
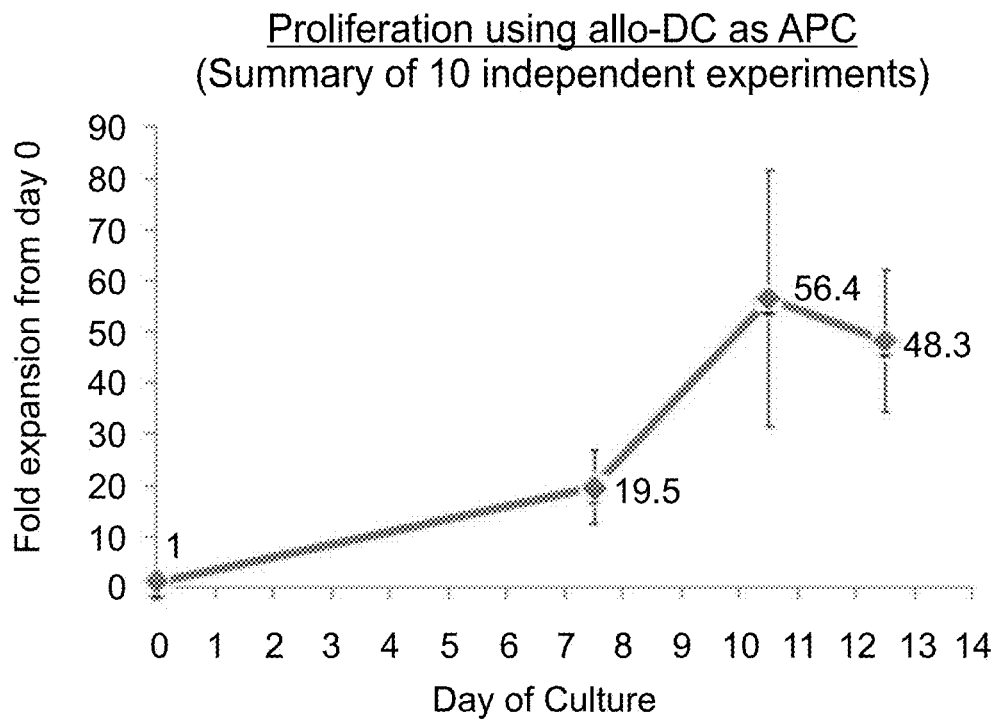
Figure 4B:
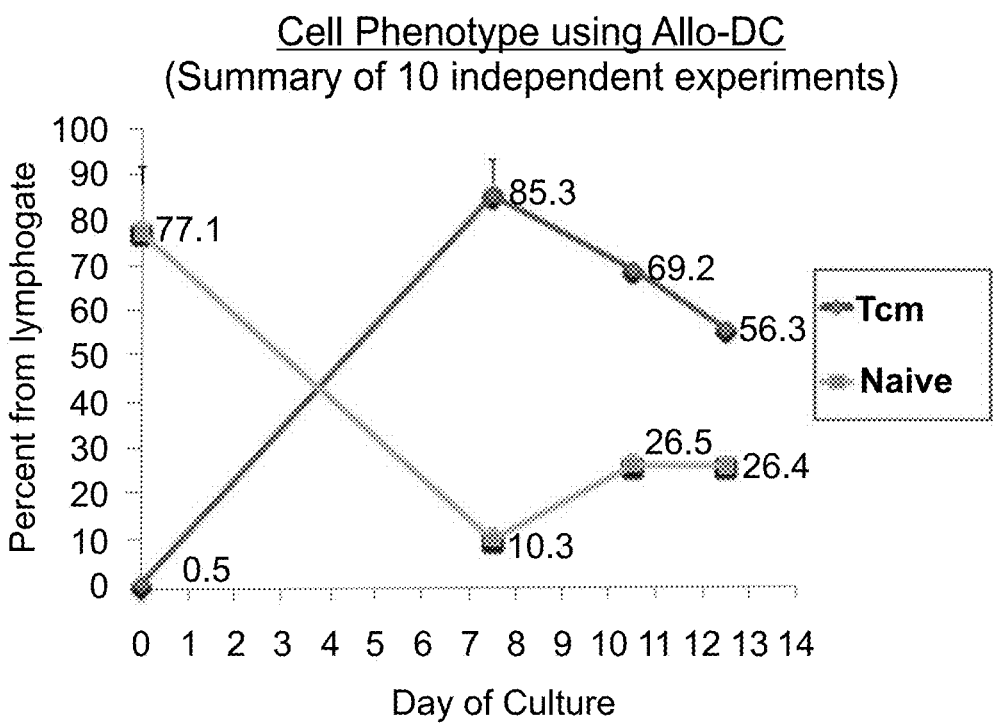

FIGS. 4A-B are graphs depicting the proliferation and cell phenotype of anti-third party T central memory cells of the present invention. FIG. 4A depicts Tcm cell proliferation from day 0 until day 12 of culture; and FIG. 4B depicts cell phenotype using the same culture against Allo-DC.

Figure 5:
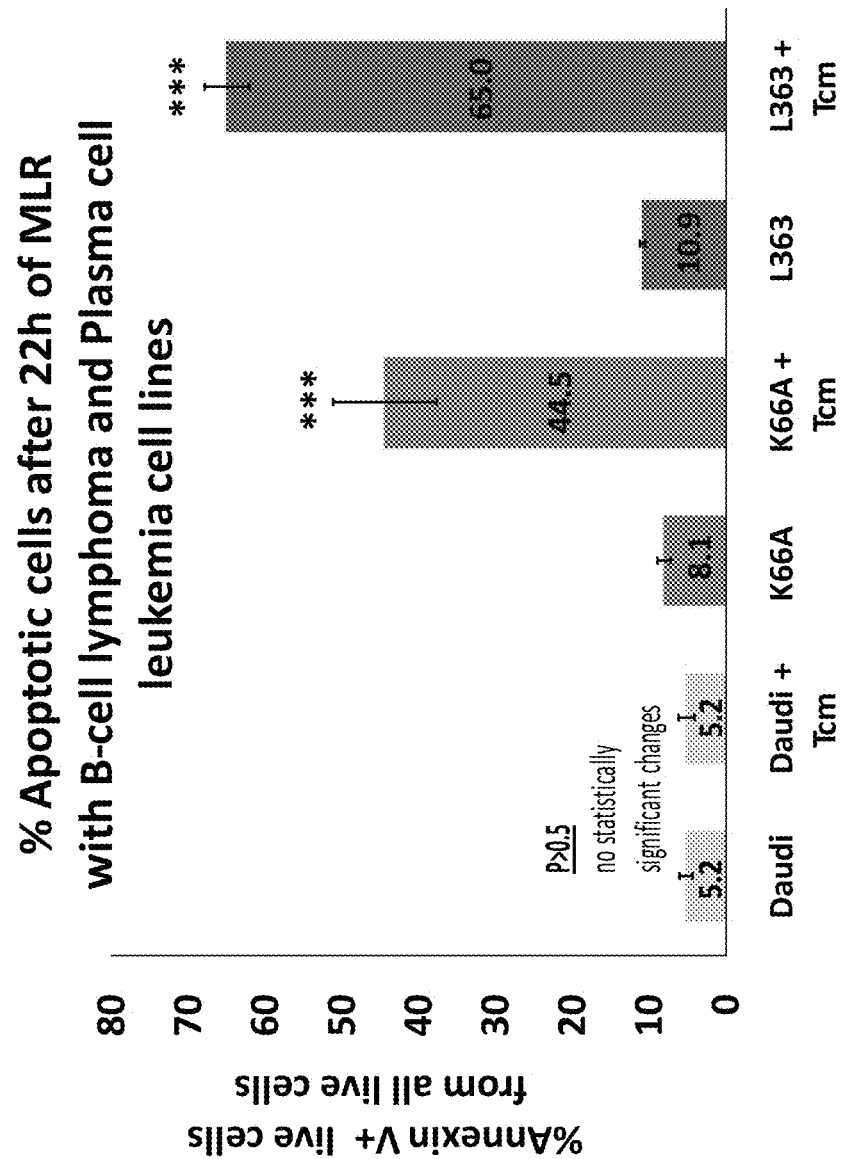

FIG. 5 is a graph depicting the percent of apoptotic cells after 22 hours of mixed lymphocyte reaction (MLR) with B-cell lymphoma and plasma cell leukemia cell lines. CalceinAM pre-labeled Daudi, H.My2 C1R HLA A2 K66A mutant or L363 cell lines were incubated for 22 hours with or without 5-fold excess of anti-$3^{rd}$ party Tcm. Annexin V+ cells were determined by FACS. Data is shown as mean±SD of pentaplicate cultures. ***p<0.001 values indicate statistically significant changes compared to samples cultured in the absence of Tcm.

Figure 6:
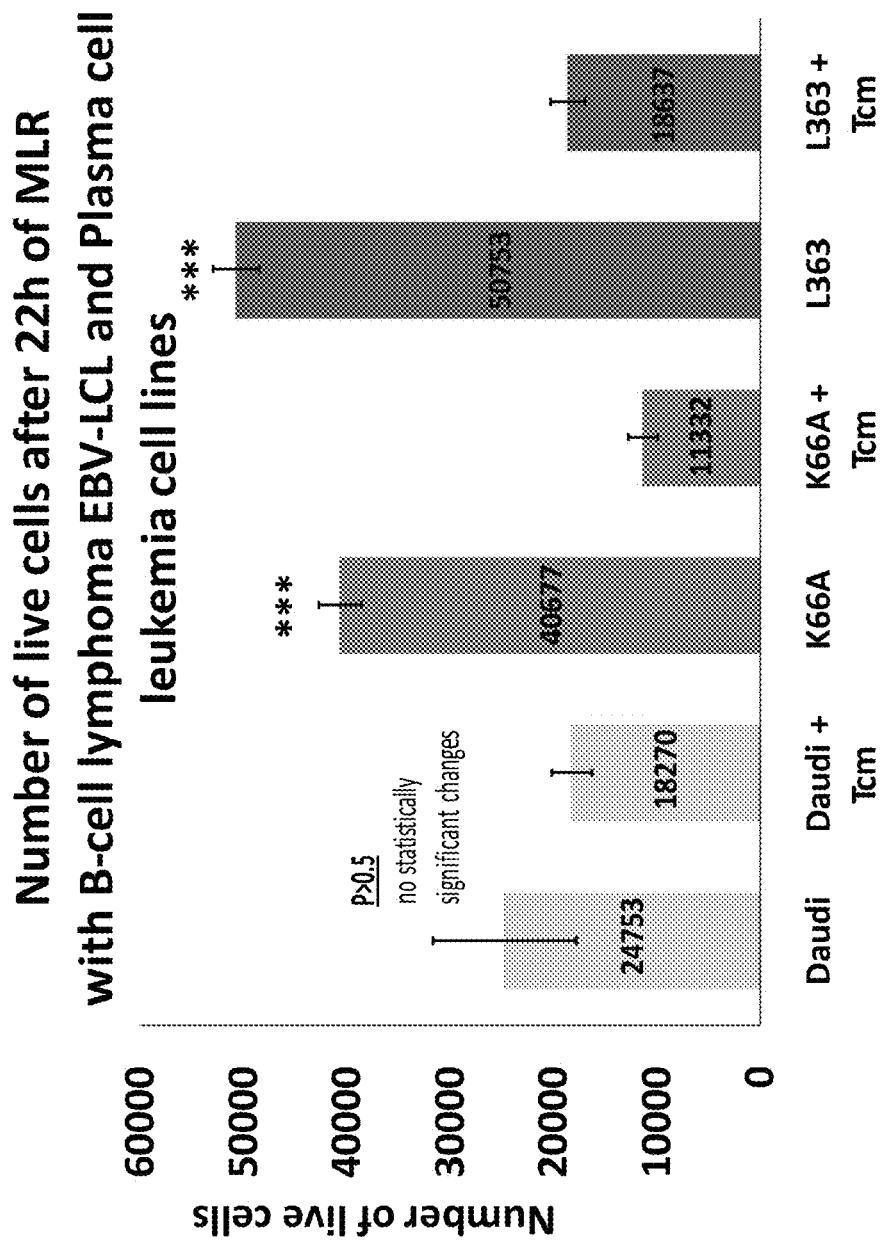

FIG. 6 is a graph depicting the number of live cells after 22 hours of mixed lymphocyte reaction (MLR) with B-cell lymphoma EBV-LCL and plasma cell leukemia cell lines. CalceinAM pre-labeled Daudi, H.My2 C1R HLA A2 K66A mutant or L363 cell lines were incubated for 22 hours with or without 5-fold excess of anti-$3^{rd}$ party Tcm. Numbers of viable CalceinAM$^+$ cells were determined by FACS. Data is shown as mean±SD of pentaplicate cultures. ***p<0.001 values indicate statistically significant changes compared to samples cultured in the absence of Tcm.

DESCRIPTION OF SPECIFIC EMBODIMENTS OF THE INVENTION

The present invention, in some embodiments thereof, relates to non-graft versus host disease (GVHD) inducing anti-third party cells comprising a central memory T-lymphocyte phenotype and, more particularly, but not exclusively, to the use of same for graft versus leukemia/lymphoma treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have uncovered that anti-3rd party CD8+ T central memory (Tcm) cells comprise in vivo graft versus leukemia/lymphoma (GVL) activity and may therefore be used to treat malignant hematopoietic diseases, such as lymphoma and leukemia.

As is shown herein below and in the Examples section which follows, the present inventors have shown GVL reactivity of anti-3rd party CD8+ Tcm cells in an in-vivo mouse model specifically designed to simulate allogeneic bone marrow transplant (BMT) in lymphoma patients. Initially, inventors confirmed in-vitro that non-alloreactive derived murine anti-3rd party Tcm cells act similarly to human anti-3rd party CTLs and directly eradicate A20 murine lymphoma cells (see Example 1 of the Examples section which follows). Subsequently, the present inventors established a minimal residual disease mouse model for B cell lymphoma utilizing A20 B cell lymphoma cell line in which luciferase reporter gene was stably integrated into its genome (A20-luc). These cells enabled sensitive monitoring of in-vivo tumor progression by bioluminescence imaging (BLI). Using this model, inventors discovered that both syngeneic and allogeneic anti-3rd party Tcm cells exhibit marked GVL reactivity without causing graft versus host disease (GVHD) when administered in conjunction with a syngeneic bone marrow transplant (Examples 2 and 3, respectively, of the Examples section which follows). Furthermore, the present inventors showed an effective GVL effect devoid of GVHD when administering allogeneic anti-3rd party Tcm cells (donor type) in conjunction with an allogeneic bone marrow transplant (Example 4, of the Examples section which follows). Taken together, all these findings substantiate the use of anti-third party Tcm cells as graft versus leukemia/lymphoma cells for eradication of diseased cells. Moreover, the present results demonstrate the ability to use anti-third party Tcm cells from a donor non-syngeneic with respect to the recipient and to the transplant donor (e.g. from two different donors).

Thus, according to one aspect of the present invention there is provided a method of treating a disease in a subject in need thereof, the method comprising: (a) transplanting a cell or tissue graft to the subject; and (b) administering to the subject a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, and further wherein the cells are either: (i) non-syngeneic with both the subject and the graft; or (ii) non-syngeneic with the graft and syngeneic with the subject, thereby treating the subject.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "subject" or "subject in need thereof" refers to a mammal, preferably a human being, male or female at any age that is in need of a cell or tissue graft. Typically the subject is in need of cell or tissue graft (also referred to herein as recipient) due to a disorder or a pathological or undesired condition, state, or syndrome, or a physical, morphological or physiological abnormality which is amenable to treatment via transplantation of a cell or tissue graft. Examples of such disorders are provided further below.

As used herein, the phrase "cell or tissue graft" refers to a bodily cell (e.g. a single cell or a group of cells) or tissue (e.g. solid tissues or soft tissues, which may be transplanted in full or in part). Exemplary tissues which may be transplanted according to the present teachings include, but are not limited to, lymphoid/hematopoietic tissues (e.g. lymph node, Peyer's patches thymus or bone marrow). Exemplary cells which may be transplanted according to the present teachings include, but are not limited to, hematopoietic stem cells (e.g. immature hematopoietic cells).

According to a specific embodiment, the hematopoietic stem cells of the present invention are CD34+.

Depending on the application, the method may be effected using a cell or tissue graft which is syngeneic or non-syngeneic with the subject.

As used herein, the term "syngeneic" refers to a cell or tissue which is derived from an individual who is essentially genetically identical with the subject. Typically, essentially fully inbred mammals, mammalian clones, or homozygotic twin mammals are syngeneic.

Examples of syngeneic cells or tissues include cells or tissues derived from the subject (also referred to in the art as "autologous"), a clone of the subject, or a homozygotic twin of the subject.

As used herein, the term "non-syngeneic" refers to a cell or tissue which is derived from an individual who is allogeneic or xenogeneic with the subject's lymphocytes (also referred to in the art as "non-autologous").

As used herein, the term "allogeneic" refers to a cell or tissue which is derived from a donor who is of the same species as the subject, but which is substantially non-clonal with the subject. Typically, outbred, non-zygotic twin mammals of the same species are allogeneic with each other. It will be appreciated that an allogeneic donor may be HLA identical or HLA non-identical with respect to the subject.

As used herein, the term "xenogeneic" refers to a cell or tissue which substantially expresses antigens of a different species relative to the species of a substantial proportion of the lymphocytes of the subject. Typically, outbred mammals of different species are xenogeneic with each other.

The present invention envisages that xenogeneic cells or tissues are derived from a variety of species such as, but not limited to, bovines (e.g., cow), equids (e.g., horse), porcines (e.g. pig), ovids (e.g., goat, sheep), felines (e.g., *Felis domestica*), canines (e.g., *Canis domestica*), rodents (e.g., mouse, rat, rabbit, guinea pig, gerbil, hamster) or primates (e.g., chimpanzee, rhesus monkey, macaque monkey, marmoset).

Cells or tissues of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

According to an embodiment of the present invention, both the subject and the donor are humans.

Depending on the application and available sources, the cells or tissue grafts of the present invention may be obtained from a prenatal organism, postnatal organism, an adult or a cadaver donor. Moreover, depending on the application needed, the cells or tissues may be naïve or genetically modified. Such determinations are well within the ability of one of ordinary skill in the art.

Any method known in the art may be employed to obtain a cell or tissue (e.g. for transplantation).

Transplanting the cell or tissue graft into the subject may be effected in numerous ways, depending on various parameters, such as, for example, the cell or tissue type; the type, stage or severity of the recipient's disease (e.g. organ failure); the physical or physiological parameters specific to the subject; and/or the desired therapeutic outcome.

Transplanting a cell or tissue graft of the present invention may be effected by transplanting the cell or tissue graft into any one of various anatomical locations, depending on the application. The cell or tissue graft may be transplanted into a homotopic anatomical location (a normal anatomical location for the transplant), or into an ectopic anatomical location (an abnormal anatomical location for the transplant). Depending on the application, the cell or tissue graft may be advantageously implanted under the renal capsule, or into the kidney, the testicular fat, the sub cutis, the omentum, the portal vein, the liver, the spleen, the bones, the heart cavity, the heart, the chest cavity, the lung, the skin, the pancreas and/or the intra abdominal space.

For example, in cases requiring immature hematopoietic cell transplantation, immature autologous, allogeneic or xenogeneic hematopoietic cells (e.g. stem cells) which can be derived, for example, from bone marrow, mobilized peripheral blood (by for example leukapheresis), fetal liver, yolk sac and/or cord blood of the syngeneic or non-syngeneic donor can be transplanted to a recipient suffering from a disease.

According to an embodiment of the present invention, the disease is a malignant disease. According to a specific embodiment, the malignant disease is a malignancy of hematopoietic or lymphoid tissues. According to another specific embodiment, the malignant disease is a B cell malignancy (i.e. involving B lymphocytes).

Such a disease includes, but is not limited to, leukemia [e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)], lymphoma [e.g., Hodgkin's lymphoma, non-Hodgkin's lymphoma, B cell, diffuse large B-cell lymphoma (DLBCL), B-cell chronic lymphocytic leukemia/lymphoma, Burkitt's lymphoma, T cell, cutaneous T cell, precursor T-cell leukemia/lymphoma, follicular lymphoma, mantle cell lymphoma, MALT lymphoma, histiocytic, lymphoblastic, thymic and Mycosis fungoides], diseases associated with transplantation of a graft (e.g. graft rejection, chronic graft rejection, subacute graft rejection, hyper-acute graft rejection, acute graft rejection and graft versus host disease), autoimmune diseases such as Type 1 diabetes, severe combined immunodeficiency syndromes (SCID), including adenosine deaminase (ADA), osteopetrosis, aplastic anemia, Gaucher's disease, thalassemia and other congenital or genetically-determined hematopoietic abnormalities.

It will be appreciated that the syngeneic or non-syngeneic hematopoietic cells (e.g. immature hematopoietic cells) of the present invention may be transplanted into a recipient using any method known in the art for cell transplantation, such as but not limited to, cell infusion (e.g. I.V.) or via an intraperitoneal route.

Optionally, when transplanting a cell or tissue graft of the present invention into a subject having a defective organ, it may be advantageous to first at least partially remove the failed organ from the subject so as to enable optimal development of the graft, and structural/functional integration thereof with the anatomy/physiology of the subject.

Following transplantation of the cell or tissue graft into the subject according to the present teachings, it is advisable, according to standard medical practice, to monitor the growth functionality and immuno-compatability of the organ according to any one of various standard art techniques. For example, structural development of the cells or tissues may be monitored via computerized tomography or ultrasound imaging while engraftment of non-syngeneic cell or bone marrow grafts can be monitored for example by chimerism testing [e.g. by PCR-based procedures using short tandem repeat (STR) analysis].

Regardless of the transplant type, to avoid graft rejection and graft versus host disease and to abolish any residual tumor cells, the method of the present invention utilizes anti-third party Tcm cells.

Thus, according to an aspect of the present invention, the subject is administered a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation.

The phrase "isolated population of cells" as used herein refers to cells which have been isolated from their natural environment (e.g., the human body).

The term "non-GVHD" as used herein refers to having substantially no graft versus host inducing reactivity. Thus, the cells of the present invention are generated as to not significantly cause graft versus host disease (GVHD).

The phrase "anti-third party cells" as used herein refers to lymphocytes (e.g. T lymphocytes) which are directed (e.g. by T cell recognition) against a third party antigen or antigens.

As used herein the phrase "third party antigen or antigens" refers to a soluble or non-soluble (such as membrane associated) antigen or antigens which are not present in either the donor or recipient, as depicted in detail infra.

According to one embodiment, the third party antigen or antigens of the present invention is selected from the group consisting of third party cells, a cell antigen, a viral antigen, a bacterial antigen, a protein extract, a purified protein and a synthetic peptide presented by autologous presenting cells, non-autologous presenting cells or on an artificial vehicle or artificial antigen presenting cell.

For example, third party antigens can be third party cells, antigens of viruses, such as for example, Epstein-Barr virus (EBV) or cyto-megalo virus (CMV) or antigens of bacteria, such as flagellin Viral or bacterial antigens can be presented by cells (e.g., cell line) infected therewith or otherwise made to express viral/bacterial proteins. Autologous or non-autologous antigen presenting cells can be used to present short synthetic peptides fused or loaded thereto. Such short peptides may be viral derived peptides or peptides representing any other antigen.

Dedicated software can be used to analyze viral or other sequences to identify immunogenic short peptides, i.e., peptides presentable in context of class I MHC or class II MHC.

Third party cells can be either allogeneic or xenogeneic with respects to the recipient (explained in further detail below). In the case of allogeneic third party cells, such cells have HLA antigens different from that of the donor but which are not cross reactive with the recipient HLA antigens, such that anti-third party cells generated against such cells are not reactive against a transplant or recipient antigens.

According to an embodiment of the present invention the allogeneic or xenogeneic third party cells are stimulatory cells such as, but not limited to, cells purified from peripheral blood lymphocytes (PBL), spleen or lymph nodes, cytokine-mobilized PBLs, in vitro expanded antigen-presenting dendritic cells (APC), B cell lines, Antigen presenting cells (APC) such as artificial APC (e.g. K562 cell line transfected with HLA and/or costimulatory molecules).

According to an embodiment, the third party antigen or antigens comprise dendritic cells.

Third party antigens can be presented on the cellular, viral or bacterial surfaces or derived and/or purified therefrom. Additionally, a viral, bacterial or any foreign antigen can be displayed on an infected cell or can be displayed on an artificial vehicle such as a liposome or an artificial APC (e.g. fibroblast or leukemic cell line transfected with the third party antigen or antigens).

In addition, third party antigens can, for example, be proteins extracted or purified from a variety of sources. An example of a purified protein which can serve as a third party antigen according to the present invention is ovalbumin. Other examples are envisaged.

Utilizing cells, viruses, bacteria, virally infected, bacteria infected, viral peptides or bacteria peptides presenting cells as third party antigens is particularly advantageous since such third party antigens include a diverse array of antigenic determinants and as such direct the formation of anti-third party cells of a diverse population, which may further serve in faster reconstitution of T-cells in cases where such reconstitution is required, e.g., following lethal or sublethal irradiation or chemotherapy procedure.

Furthermore, when anti-third party cells are directed against third party antigens, it is of advantage to obtain at least some graft versus disease (e.g. cancer cell such as graft versus leukemia) activity due to TCR independent killing mediated by LFA1-ICAM1 binding [Arditti et al., Blood (2005) 105 (8):3365-71. Epub 2004 Jul. 6].

According to some embodiments, the anti-third party cells of the present invention comprise a central memory T-lymphocyte (Tcm) phenotype.

The phrase "central memory T-lymphocyte (Tcm) phenotype" as used herein refers to a subset of T cytotoxic cells which home to the lymph nodes. Cells having the Tcm phenotype, in humans, typically express CD8+/CD62L+/CD45RO+/L−selectin+/CD45RA−. According to a more specific embodiment the Tcm phenotype comprises a CD8+/CD62L+ signature. It will be appreciated that Tcm cells may express all of the signature markers on a single cell or may express only part of the signature markers on a single cell.

It will be appreciated that at least at least 30%, at least 40%, at least 50%, at least 55%, at least 60%, at least 65%, at least 70%, at least 75%, at least 80%, at least 85%, at least 90%, at least 95% or at least 100% of the isolated population of cells comprise cells having the Tcm cell signature.

As mentioned, the Tcm cells typically home to the lymph nodes following transplantation. According to some embodiments the anti-third party Tcm cells of the present invention may home to any of the lymph nodes following transplantation, as for example, the peripheral lymph nodes and mesenteric lymph nodes. The homing nature of these cells allows them to exert their tolerance effect in a rapid and efficient manner.

Thus, the anti-third party Tcm cells of the present invention are tolerance-inducing cells.

The phrase "tolerance inducing cells" as used herein refers to cells which provoke decreased responsiveness of the recipient's cells (e.g. recipient's T cells) when they come in contact with same. Tolerance inducing cells include veto cells (i.e. T cells which lead to apoptosis of host T cells upon contact with same) as was previously described in PCT Publication Nos. WO 2001/049243 and WO 2002/102971.

The use of tolerance inducing cells is especially beneficial in situations in which there is a need to eliminate graft rejection and overcome graft versus host disease (GVHD), such as in transplantation of allogeneic or xenogeneic cells or tissues.

According to some embodiments, the Tcm cells of the present invention may be naïve cells (e.g. non-genetically modified) or genetically modified cells (e.g. cells which have been genetically engineered to express or not express specific genes, markers or peptides or to secrete or not secrete specific cytokines). Any method known in the art may be implemented in genetically engineering the cells, such as by inactivation of the relevant gene/s or by insertion of an antisense RNA interfering with polypeptide expression (see e.g. WO/2000/039294, which is hereby incorporated by reference).

Any method used for the generation of anti-third party non-alloreactive cells (devoid of graft versus host (GVH) activity) can be used in accordance with the present teachings.

The anti-third party Tcm cells of the present invention are typically generated by first contacting syngeneic or non-syngeneic peripheral blood mononuclear cells (PBMC) with a third party antigen or antigens (such as described above) in a culture deprived of cytokines (i.e., without the addition of cytokines). This step is typically carried out for about 12-72 hours, 24-48 hours, 1-10 days, 1-7 days, 1-5 days, 2-3 days or 2 days and allows elimination of GVH reactive cells (e.g. T cells). Alternatively, the anti-third party Tcm cells may be generated devoid of graft versus host (GVH) activity by supplementing the otherwise cytokine-free culture with IL-21 (0.001-3000 ng/ml, 10-1000 ng/ml, 10-100 ng/ml, 1-100 ng/ml, 0.1-100 ng/ml, 0.1-10 ng/ml, 1-50 ng/ml or 1-10 ng/ml). This step is typically carried out for about 12-72 hours, 24-48 hours, 1-10 days, 1-10 days, 1-7 days, 1-5 days, 2-3 days or 3 days.

Next, the anti-third party cells are cultured in the presence of IL-15 (0.05-500 ng/ml, 0.001-3000 ng/ml, 10-1000 ng/ml, 10-100 ng/ml, 1-100 ng/ml, 0.1-100 ng/ml, 0.1-10 ng/ml, 1-50 ng/ml or 1-10 ng/ml. According to a specific embodiment the concentration is 5 ng/ml) for a period of about 3-30 days, 6-30 days, 3-20 days, 10-20 days, 3-15 days, 5-15 days, 7-15 days, 7-14 days, 3-10 days, 3-7 days or 14 days in an antigen-free environment. The culture may be further effected in the presence of additional cytokines such as IL-7 (0.05-500 ng/ml, 0.001-3000 ng/ml, 10-1000 ng/ml, 10-100 ng/ml, 1-100 ng/ml, 0.1-100 ng/ml, 0.1-10 ng/ml, 1-50 ng/ml or 1-10 ng/ml. According to a specific embodiment the concentration is 5 ng/ml) and/or IL-21 (0.001-3000 ng/ml, 0.001-3000 ng/ml, 10-1000 ng/ml, 10-100 ng/ml, 1-100 ng/ml, 0.1-100 ng/ml, 0.1-10 ng/ml, 1-50 ng/ml or 20-50 ng/ml. According to a specific embodiment the concentration is 30 ng/ml). This process enables proliferation of anti-third party cells comprising a central memory T-lymphocyte (Tcm) phenotype and being deprived of GVHD reactivity.

It will be appreciated that an additional step which allows selection of $CD8^+$ T cells may be carried out, such as by the use of MACS beads, before culturing the cells in the presence of IL-15. Such a step may be beneficial in order to increase the purity of the $CD8^+$ cells within the culture (i.e. eliminate other lymphocytes within the cell culture e.g. T $CD4^+$ cells) or in order to increase the number of $CD8^+$ T cells. Thus, isolation of CD8+ cells can be done prior to culturing with the third party antigen or antigens or following culturing with the third party antigen or antigens and prior to culturing with CD15.

According to some embodiments of the invention, syngeneic PBMCs (e.g. from the subject) may be used according to the present teachings (i.e. in situations when syngeneic Tcm cells may be beneficial for treatment). Likewise, non-syngeneic PBMCs (e.g. allogeneic or xenogeneic with respect to the subject) may be used according to the present teachings. The source of the PBMCs will be determined with respect to the intended use of the cells (see further details hereinbelow) and is well within the capability of one skilled in the art, especially in light of the detailed disclosure provided herein.

As described in detail in the Examples section which follows, the present inventors have shown that the anti-third party Tcm cells may be of the same origin as the cell or tissue graft (e.g. bone marrow cells), specifically, they may both be derived from a syngeneic donor (e.g. from the subject, see Example 2 and FIGS. 1A-I) or may both be derived from a non-syngeneic donor (e.g. from an allogeneic donor, see Example 4 and FIGS. 3A-I). Conversely, the anti-third party Tcm cells may be from a different origin compared to the cell or tissue graft (e.g. the bone marrow cells may be from the subject and the anti-third party cells may be from an allogeneic donor, Example 3 and FIGS. 2A-G).

Thus, according to an embodiment of the present invention, the anti-third party Tcm cells may be non-syngeneic (e.g. allogeneic or xenogeneic) with both the subject and the graft.

As used herein, the phrase "non-syngeneic with both the subject and the graft" when relating to anti-third party Tcm cells of the present invention qualifies the anti-third party Tcm cells as being allogeneic or xenogeneic with the subject, and allogeneic or xenogeneic with the graft in any combination. Thus, the anti-third party Tcm cells may be obtained from an origin different from the subject and from the graft donor.

According to a specific embodiment, the anti-third party Tcm cells are non-syngeneic with both the subject and the graft (e.g. from a second donor).

According to another embodiment, the anti-third party Tcm cells may be non-syngeneic with respect to only the subject. According to another embodiment, the anti-third party Tcm cells may be non-syngeneic with respect to only the cell or tissue graft.

According to one embodiment, the anti-third party Tcm cells are non-syngeneic with the graft and syngeneic with the subject (e.g. of an autologous origin in situations in which the graft is of a non-autologous origin).

According to a specific embodiment, when the graft comprises immature hematopoietic cells which are non-syngeneic with the subject (e.g. non-autologous), the isolated population of cells are syngeneic with the subject (e.g. autologous).

As used herein, the term "immature hematopoietic cells" refers to any type of incompletely differentiated cells which are capable of differentiating into one or more types of fully differentiated hematopoietic cells. Immature hematopoietic cells include without limitation types of cells referred to in the art as "progenitor cells", "precursor cells", "stem cells", "pluripotent cells", "multipotent cells", and the like.

Preferably the immature hematopoietic cells are hematopoietic stem cells.

Preferably, where the immature hematopoietic cells are derived from a human, the immature hematopoietic cells are CD34+ cells, such as CD34+CD133+ cells.

Types of grafts of the present invention which comprise immature hematopoietic cells include whole bone marrow cell grafts (T-cell depleted or non-T-cell-depleted), grafts of immature hematopoietic cells from bone marrow aspirates, grafts of peripheral blood-derived immature hematopoietic cells and grafts of umbilical cord-derived immature hematopoietic cells. Methods of obtaining such grafts are described hereinbelow.

A graft which comprises human peripheral blood-derived hematopoietic stem cells may be obtained according to standard methods, for example by mobilizing CD34+ cells into the peripheral blood by cytokine treatment of the donor, and harvesting of the mobilized CD34+ cells via leukapheresis. Ample guidance is provided in the literature of the art for practicing isolation of bone marrow-derived stem cells from the bone marrow or the blood (refer, for example, to: Arai S, Klingemann H G., 2003. Arch Med Res. 34:545-53; and Repka T. and Weisdorf D., 1998. Curr Opin Oncol. 10:112-7; Janssen W E. et al., 1994. Cancer Control 1:225-230; Atkinson K., 1999. Curr Top Pathol. 92:107-36).

A graft of human umbilical cord blood-derived hematopoietic stem cells may be obtained according to standard methods (refer, for example, to: Quillen K, Berkman E M., 1996. J. Hematother. 5:153-5).

A graft of hematopoietic stem cells of the present invention may also be derived from liver tissue or yolk sac.

A requisite number of hematopoietic stem cells can be provided by ex-vivo expansion of primary hematopoietic stem cells (reviewed in Emerson, 1996, Blood 87:3082, and described in more detail in Petzer et al., 1996, Proc. Natl. Acad. Sci. U.S.A. 3:1470; Zundstra et al., 1994, BioTechnology 12:909; and WO 95 11692). According to another specific embodiment, when the graft comprises immature hematopoietic cells which are non-syngeneic with the subject (e.g. non-autologous), the isolated population of cells are non-syngeneic with both the subject and with the graft. (e.g. the immature hematopoietic cells and the isolated population of cells are from different donors).

According to another embodiment, there is provided a method of treating a disease in a subject in need thereof, the method comprising: (a) transplanting immature hematopoietic cells to the subject; and (b) administering to the subject a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, wherein when the immature hematopoietic cells are syngeneic with the subject, the isolated population of cells are selected syngeneic with the subject or non-syngeneic with the subject.

According to a specific embodiment, both the immature hematopoietic cells and the isolated population of cells are autologous (e.g. from the subject).

According to another specific embodiment, the immature hematopoietic cells are autologous (e.g. from the subject) and the isolated population of cells are non-autologous (e.g. from a donor).

According to another embodiment, there is provided a method of treating a disease in a subject in need thereof, the method comprising: (a) transplanting immature hematopoietic cells to the subject; and (b) administering to the subject a therapeutically effective amount of an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, wherein when the immature hematopoietic cells are non-syngeneic with the subject, the isolated population of cells are selected syngeneic with the subject or non-syngeneic with both the subject and the immature hematopoietic cells.

According to a specific embodiment, the immature hematopoietic cells are non-autologous (e.g. from a donor) and the isolated population of cells are autologous (e.g. from the subject).

According to another embodiment, when the immature hematopoietic cells are non-syngeneic with the subject (e.g. non-autologous), the anti-third party Tcm cells are non-syngeneic with both the subject and the graft (e.g. two different donors).

According to a specific embodiment, the immature hematopoietic cells and the isolated population of cells are from different donors.

According to an additional aspect of the present invention, there is provided an isolated population of cells comprising non-graft versus host (GVHD) inducing anti-third party cells having a central memory T-lymphocyte (Tcm) phenotype, the cells being tolerance-inducing cells and capable of homing to the lymph nodes following transplantation, and further wherein the cells are non-syngeneic with both a subject and a cell or tissue graft.

(i) non-syngeneic with both a host subject and a graft; or
(ii) non-syngeneic with a graft and syngeneic with a host subject.

According to one embodiment, the cells non-syngeneic with the graft and syngeneic with the host subject are autologous.

Thus, the present invention contemplates administration to a subject any anti-third party Tcm cells (e.g. non-syngeneic with both the subject and the graft or non-syngeneic with the graft and syngeneic with the subject) which will result in eradication of a disease (e.g. leukemia or lymphoma) and will concomitantly enhance engraftment of a cell or tissue transplant (e.g. autologous or non-autologous bone marrow cells) by being tolerogenic cells and non-GVHD.

It will be appreciated that the anti-third party cells may be administered concomitantly with a cell or tissue graft (e.g. as an adjuvant therapy), may be administered prior to transplantation of a cell or tissue graft (e.g. in order to eradicate residual cancer cells prior to transplantation and to eliminate graft rejection and graft versus host disease), or may be administered following transplantation of a cell or tissue graft (e.g. in order to eradicate residual cancer cells following transplantation and to eliminate graft rejection and graft versus host disease).

It will be appreciated that the anti-third party cells may be administered at any time following transplantation. Typically, the anti-third party Tcm cells are administered on day 0, day 1, day 2, day 3, day 4, day 5, day 6, day 7, day 8 or day 10 following transplantation. However, the anti-third party Tcm cells may be administered extended times after transplantation, as for example, two weeks, a month, 2 months, 3 months, 4 months, 5 months, 6 months, 7 months, 8 months, 9 months, 10 months, 11 months, 12 months, 18 months or 24 months following transplantation.

The anti third party Tcm cells may be administered via any method known in the art for cell transplantation, such as but not limited to, cell infusion (e.g. I.V.) or via an intraperitoneal route.

Without being bound to theory, a therapeutically effective amount is an amount of anti-third party Tcm cells efficient for tolerization, anti-tumor effect and/or immune reconstitution without inducing GVHD. Since the Tcm cells of the present invention home to the lymph nodes following transplantation, lower amounts of cells (compared to the dose of cells previously used, see for example WO 2001/049243) may be needed to achieve the beneficial effects of the cells (e.g. tolerization, anti-tumor effect and/or immune reconstitution). It will be appreciated that lower levels of immunosuppressive drugs may be needed in conjunction with the Tcm cells of the present invention (such as exclusion of rapamycin from the therapeutic protocol).

Determination of the therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

For example, in case of tissue graft the number of anti-third party Tcm cells infused to a recipient should be more than $1\times10^4$/Kg body weight. The number of anti-third party Tcm cells infused to a recipient should typically be in the range of $1\times10^4$/Kg body weight to $1\times10^9$/Kg body weight.

In order to facilitate engraftment of the cell or tissue graft, the method may further advantageously comprise conditioning the subject with an immunosuppressive regimen prior to, concomitantly with, or following transplantation of the cell or tissue graft.

Thus, according to an embodiment of the present invention, the subject is conditioned under sublethal, lethal or supralethal conditions prior to transplantation of a cell or tissue graft.

For example, the subject may be treated with a myeloablative or non-myeloablative conditioning. The type of conditioning may be determined by one of ordinary skill in the art and takes into account the age and disease severity of the subject. Thus, for example, an elderly subject (e.g. one who is over 40 years of age) may be treated with a mild immunosuppressive regimen.

Examples of suitable types of immunosuppressive regimens include administration of immunosuppressive drugs, tolerance inducing cell populations (as described in detail hereinabove), and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Preferably, the immunosuppressive regimen consists of administering at least one immunosuppressant agent to the subject.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Animals

Female 6 to 12 week old BALB/c, CB6 (F1), FVB, C57BL/6, and BALB/c-NUDE mice were obtained from Harlan Laboratories. Progeny of B6-NUDE mice were bred at the Weizmann Institute Animal Center. All mice were kept in small cages (5 animals in each cage) and fed sterile food and acid water. All studies were approved by the Weizmann Institute of Science Institutional Animal Care and Use Committee.

Cells

The A20 murine lymphoma cell line, a BALb/c ($H-2^d$) derived B cell lymphoma/leukemia line, previously described [Kim K J et al., J. Immunol. (1979) 122: 549-554], and the stable transfectant of A20, the A20 yfp/luc$^+$, previously described [Edinger M et al., Blood. (2003) 101: 640-648] were both maintained in RPMI 1640 medium supplemented with 5% FCS, 2 mM glutamine, nonessential amino acids, antibiotics, and 50 µM 2-βmercaptoethanol.

Preparation of Host Nonreactive Anti-3$^{rd}$-Party Tcm

Anti-third-party Tcm were prepared as previously described [Ophir E et al., Blood (2010) 115: 2095-2104] briefly, splenocytes of the donor mice were cultured against irradiated third-party splenocytes for 60 hours under cytokine deprivation. Subsequently, CD8$^+$ cells were positively selected using Magnetic Particles (BD Pharmingen) and cultured in an Ag-free environment. rhIL-15 (20 ng/mL; R&D Systems) was added every second day. To attain a purified population at the end of the culture (day 16), the Tcm cells were positively selected for CD62L expression by magnetic-activated cell sorting [MACS, Milteny, Bergisch Gladbach, Germany].

Flow Cytometric Analysis

Fluorescence-activated cell sorting (FACS) analysis was performed using a modified Becton Dickinson FACScan. Cells were stained with labeled antibodies specific for CD8-phycoerythrin (PE)/fluorescein isothiocyanate (FITC)/allophycocyanin (APC) (BD Pharmingen), CalceinAM (Molecular Probes, INC., Eugene, Oreg., USA). Annexin V and 7-amino-actinomycin D (7AAD) staining were done according to the manufacturer's instructions (BD Pharmingen).

MLR Culture and Cytotoxicity Assay

Anti-3$^{rd}$-party Tcm and lymphoma cells were obtained by Ficoll density gradient centrifugation and lymphoma cells were labeled with 0.15 μg/ml CalceinAM (Molecular Probes, INC., Eugene, Oreg., USA) according to manufacturer's instructions and brought to a concentration of 1×10$^6$ cells/ml in the required media. 3×10$^5$ of the lymphoma cells were incubated with anti-3$^{rd}$-party CTLs according to the indicated ratios and time intervals for 24-well plates. Cells were recovered and analyzed for survival using surface markers such as Annexin-V (BD) and by measuring the number of CalceinAM stained lymphoma cells by FACS.

Detection of Apoptosis by Annexin V Staining

Annexin V APC was used to detect apoptotic cells. Samples from in-vitro cultures were incubated with a mixture of selected monoclonal antibodies labeled with different fluorochromes for 20 minutes at 4° C. After washing off the unbound free antibody using an Annexin-V binding buffer, samples were supplemented with 5 μl AnnexinV-APC (BD). Cells were then incubated at room temperature for 15 minutes in the dark and washed with an Annexin-V binding buffer. Samples were analyzed by FACS for live cells that are positively stained of AnnexinV.

Minimal Residual Disease In-Vivo Model 12 week old BALB/c female recipient mice were exposed to a single dose of 8 Gy total body irradiation (TBI) from a Gamma beam 150-A 60 Co source (manufactured by the Atomic Energy of Canada, Kanata, ON, Canada) (day −1). On the following day (day 0) recipient mice were intravenously infused with 3×10$^6$ T cell depleted bone marrow from BALb/c-Nude mice (syngeneic) or with 3×10$^6$ T cell depleted bone marrow from B6-Nude mice, supplemented with 5×10$^3$ A20 luc lymphoma cells per mouse. On the subsequent day (day +1) mice received or did not receive 10×10$^6$ BALB/c derived anti-3$^{rd}$-party Tcm (syngeneic) or 5×10$^6$ C57BL/6 derived anti-3$^{rd}$-party Tcm (allogeneic), intravenously. Tumor localization, migratory patterns of A20 cells and the anti-lymphoma reactivity of anti-3$^{rd}$-party CTLs was surveyed using an in-vivo imaging system.

In-Vivo Imaging.

Mice were anaesthetized with Ketamine (100 mg/kg intraperitoneally (i.p) (Kepro Holand Netherlands) and Xylazine (Kepro Holand Netherlands) (20 mg/Kg i.p), and an aqueous solution of D Luciferin (150 mg/Kg i.p) (Cat#XR-1001, 30 mg/ml in PBS; Xenogen) was injected 10 minutes prior to imaging. Animals were placed into the light-tight chamber of the In Vivo Imaging system (IVIS® 100, Xenogen) coupled with a Pixelfly QE (PCO, K, Germany) charge-coupled device (CCD) camera at the Department of Veterinary Resources of the Weizmann Institute. A grayscale body surface reference image (digital photograph) was taken after a 10 second exposure, under strong illumination. Image data processing and analysis were performed using Living Image 2.5 software. The mice were monitored for tumor growth from day 14 on weekly intervals.

Statistical Analysis

The analysis of survival data was performed using Kaplan-Meier curves (log-rank test). Comparison of means was conducted using the Student t test.

Example 1

Establishment of a Mouse Model

To establish an appropriate mouse model, inventors initially verified that anti-3$^{rd}$ party Tcm cells derived from (B6×BALB/c)F1 exhibit TCR independent killing of A20 lymphoma cells of BALB/c origin (34.8±12.1% in 4 experiments, 5:1 Tcm/lymphoma cell ratio, in comparison to A20 cells incubated without Tcm, p<0.05). Moreover, after 16 hours of incubation with Tcm cells, AnnexinV staining of A20 cells was significantly enhanced compared to basal staining level (14.8±4.5% and 5.2±2.2% respectively, in 3 experiments, p<0.05), suggesting an apoptosis based mechanism, similar to that previously described for killing of human lymphoma cells [Lask A et al. (submitted 2010); Arditti F D et al., Blood (2005) 105:3365-3371].

Example 2

Treatment Protocol by Syngeneic Bone Marrow Transplant and Tcm Cells

Using luciferase expressing A20 cells, inventors were able to follow the fate of the malignant cells in vivo, and study the anti-lymphoma effect of added donor anti-3$^{rd}$ party Tcm to either syngeneic or allogeneic bone marrow transplant (BMT, hereinbelow), in a model simulating minimal residual disease. In the syngeneic model, 3×10$^6$ Nude BALB/c BM cells were transplanted into lethally irradiated BALB/c mice together with 5000 A20 cells. On the next day, syngeneic Tcm were infused. As can be seen in FIGS. 1A-D, none of the untreated mice survived (0/7) 100 days post bone marrow transplant (BMT, 23 days median survival). However, administration of 1×10$^7$ or 2×10$^7$ syngeneic Tcm cells led to significantly diminished tumor burden (FIGS. 1E-H) and improved overall survival of 28% of mice (2/7, P<0.0001) and 40% of mice (2/5, P<0.002) 100 days post BMT, with median survival of 49 and 80 days, respectively (FIG. 1I).

Example 3

Treatment Protocol by Syngeneic Bone Marrow Transplant and Allogeneic Tcm Cells

An earlier study performed in our lab [Ophir E. et al., Blood (2010) 115: 2095-2104] showed that anti-3$^{rd}$ party Tcm cells are endowed with tolerizing activity, translated into prolonged persistence following BMT, even when using partially matched donors. Inventors therefore tested in the above described syngeneic BMT model the anti-lymphoma effect of 2×10$^7$ F1 (CB6) derived Tcm cells, replacing the syngeneic Tcm cells administered previously. Although these F1 derived Tcm cells were expected to be rejected due to MHC disparity, they were continuously present and not rejected even 2 month after transplantation (data not shown). Their long term persistence was probably the result of their tolerizing activity described above. The significant clinical effect of these F1 derived Tcm cells was demonstrated by an improved overall survival of 57.1% mice (4/7, FIGS. 2D-G) in comparison to 0% mice (0/5, FIGS. 2A-C and 2G) survival in the untreated group. Thus, these results conclusively demonstrate that anti-3$^{rd}$ party Tcm cells, derived from allogeneic donors, may be used as anti-B cell malignancy cell therapy, either alone or combined with bone marrow cells.

Example 4

Treatment Protocol by Allogeneic Bone Marrow Transplant and Allogeneic Tcm Cells When examined in the allogeneic settings, further improvement of tumor eradication was exhibited. This effect was probably due to residual alloreactivity which provided an additional graft versus leukemia/lymphoma (GVL) effect over the newly discovered T cell receptor (TCR) independent cell killing. Significantly, this additive effect was achieved without causing GVHD. In this allogeneic model, $3\times10^6$ allogeneic Nude B6 BM cells were transplanted together with 5000 A20 cells into lethally irradiated BALB/c mice. On the following day, mice were treated with donor type Tcm. Similar to the results in the syngeneic model (described in Examples 2 and 3, above), none of the untreated mice survived 100 days post BMT (0/8, 23 days median survival, FIGS. 3A-D and 3I), while administration of $5\times10^6$ donor type Tcm cells, led to remarkable overall survival of 100% (7/7) 100 days post BMT (FIGS. 3E-I). Although the allogeneic Tcm cells displayed enhanced GVL activity compared to syngeneic Tcm cells, this effect was not associated with any manifestation of GVHD. Thus, as previously described, the weight and overall appearance of mice receiving allogeneic anti-$3^{rd}$ party Tcm cells were the same as that of mice in the control group, radio-protected with a transplant of Nude BM alone.

Collectively, the present inventors demonstrated for the first time, by in vivo imaging, the GVL reactivity of murine anti-$3^{rd}$ party Tcm. These results suggest that anti-$3^{rd}$ party Tcm cells can provide a 'double supportive effect' by promoting both BM engraftment, and concurrently inducing GVL reactivity without causing GVHD. Such cell therapy is highly attractive, in particular for elderly patients with B-CLL and other B cell malignancies who might not tolerate aggressive conditioning, and can be potentially developed into an 'off the shelf' readily available product, to be used as an anti-cancer cell therapy.

Example 5

Generation of Anti-Third Party T Central Memory Cells

Materials and Experimental Procedures
Enrichment of Naïve CD8+ T Cell Cells
Peripheral blood mononuclear cells (PBMCs) were obtained by Ficoll density gradient centrifugation of buffy coats from healthy donors. Donor's PBMCs were then transferred to a 10% DMSO freezing solution and were cryopreserved in liquid nitrogen.

On day −2: Donor's Frozen PBMCs were thawed quickly in a 37° C. water bath and transferred to warm thawing medium (Cellgro DC supplemented with 10% human serum and Pen/Strep medium supplemented with Benzonase® Nuclease to avoid cell clump formation as a result of dying cells). Thawed donor's PBMCs were washed twice with warm thawing medium. In order to deplete adherent cells, donor's PBMCs were then resuspended in culture medium (Cellgro DC supplemented with 5% human Serum and Pen/Strep and 10 ng/ml IL-7) and were plated on specially coated 6-well plates for overnight incubation at 37° C.

On day −1: Non-adherent cells were removed (this process increased the concentration of the desires T cell, by removing the adhered monocytes and in addition allowed the thawed cells to recover from the thawing process before being subjected to the magnetic enrichment process).

On day 0: Untouched CD8+ T-cells were isolated using the CD8 isolation kit from Miltenyi in accordance with the manufacturer's protocol. Thereafter, CD8 T cells with naïve phenotype were obtained from the total CD8 population by depleting cells expressing the activation marker CD45RO using CD45RO magnetic beads.

Generation of Monocyte Derived Dendritic Cells (DCs)
Monocyte derived DCs were generated from allogeneic cryopreserved PBMC. The monocytes were enriched from the PBMC by plastic adherence and cultured in GM-CSF and IL-4 over the course of 3 days. Maturation was induced over the final 24 hours of culture with the addition of LPS and IFN-γ.

Generation of Anti-Third Party Tcm Cells (Naïve CD8 T Cells Targeting Monocyte Derived DCs)
Naïve CD8+ T cells were activated with irradiated (30 gy) monocyte derived DCs at a ratio of 1:0.25, in culture medium (Cellgro DC supplemented with 5% humaSerum and Pen/Strep) supplemented with IL-21 for 3 days. Thereafter, the CD8+ T cells received no further activation and were grown with IL-7 and IL-15 until day 12.

Results
On day 11 of culture, cell composition and cell phenotype was evaluated using FACS analysis and cell number was determined by trypan blue exclusion. The results indicated that the cell composition (from Lymphogate, data not shown) comprised predominantly of 94.6% CD8+ T cells (CD3+CD8+), with traces of 1.2% CD56+ NK cells (CD3-CD56+) and 1.1% NK T cell (CD3+CD56+). Furthermore, the CD8+ T cells comprised largely of 76% Tcm cells, 9% Naïve cells, 8.5% Teff/Tem and 6.5% Temra.

Example 6

Tcm Graft Versus Leukemia (GVL) Assay

Materials and Experimental Procedures
GVL Assay
B cell lines were labeled with 0.15 μg/ml CalceinAM, a vital dye that is released upon cell death, according to manufacturer's instructions. Next, $0.3\times10^6$ Calcein labeled cell lines were incubated with or without $1.5\times10^6$ anti-$3^{rd}$ party Tcm for 22 hours in 24 well plates. No exogenous cytokines were added to the MLR. After 22 hours Cells were recovered and analyzed for survival by measuring the number of surviving Calcein stained cells by FACS.

To obtain absolute values of cells, samples were suspended in constant volume and flow cytometric counts for each sample were obtained during a constant, predetermined period of time and were compared with flow cytometric counts obtained with fixed volume and fixed numbers of input cells.

Detection of Apoptosis
For Detection of apoptosis by AnnexinV staining samples were incubated with 5 μl AnnexinV-APC (BD) for 10 minutes at room temperature. Subsequently, unbound AnnexinV was washed out, and samples were analyzed by FACS.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a disease selected from the group consisting of a malignant disease, a disease associated with transplantation of a graft and an autoimmune disease, in a subject in need thereof, the method comprising:
   (a) transplanting immature hematopoietic cells to the subject; and
   (b) administering to the subject a therapeutically effective amount of an isolated population of cells comprising non-graft versus host (GVHD) inducing anti-third party cells having a central memory T-lymphocyte (Tcm) phenotype, said cells being tolerance-inducing cells and capable of homing to the lymph nodes following transplantation, wherein when said immature hematopoietic cells are syngeneic with the subject, said isolated population of cells are selected syngeneic with the subject or non-syngeneic with the subject.

2. The method of claim 1, wherein said immature hematopoietic cells and said isolated population of cells are autologous.

3. The method of claim 1, wherein said immature hematopoietic cells are autologous and said isolated population of cells are non-autologous.

4. The method of claim 1, where said subject is a human subject.

5. The method of claim 1, wherein said malignant disease comprises a malignancy of hematopoietic tissues.

6. The method of claim 1, wherein said malignancy of hematopoietic tissues comprises a lymphoma or a leukemia.

7. The method of claim 1, wherein said subject is further conditioned under sublethal, lethal or supralethal conditioning prior to (a).

8. The method of claim 1, wherein (a) and (b) are effected concomitantly.

9. The method of claim 1, wherein (b) is effected prior to (a).

10. The method of claim 1, wherein (b) is effected one day after (a).

11. The method of claim 1, wherein said central memory T-lymphocyte (Tcm) phenotype comprises a $CD8^+/CD62L^+$ signature.

12. The method of claim 11, wherein at least 50% of the isolated population of cells have said signature.

13. The method of claim 1, wherein said lymph nodes comprise peripheral lymph nodes or mesenteric lymph nodes.

14. The method of claim 1, wherein said anti-third party cells having a central memory T-lymphocyte (Tcm) phenotype, said cells being tolerance-inducing cells and capable of homing to the lymph nodes following transplantation are generated by:
   (a) contacting peripheral blood mononuclear cells (PBMC) with a third party antigen or antigens in the presence of IL-21 under conditions which allow elimination of GVH reactive cells; and
   (b) culturing said cells resulting from step (a) in the presence of IL-15 in an antigen free environment under conditions which allow proliferation of cells comprising said central memory T-lymphocyte (Tcm) phenotype, thereby generating the isolated population of cells.

15. The method of claim 14, wherein said conditions which allow elimination of GVH reactive cells comprise 1-5 days of culture.

16. The method of claim 14, wherein said third party antigen or antigens is selected from the group consisting of third party cells, a cell antigen, a viral antigen, a bacterial antigen, a protein extract, a purified protein and a synthetic peptide presented by autologous presenting cells, non-autologous presenting cells or on an artificial vehicle or artificial antigen presenting cell.

17. The method of claim 14, wherein said conditions which allow proliferation of cells further comprise IL-7 and/or IL-21.

18. The method of claim 14, wherein said culturing in the presence of IL-15 is effected for 3-30 days.

19. The method of claim 14, wherein said conditions which allow proliferation of cells comprise culturing for 3-10 days.

* * * * *